US012150951B2

(12) United States Patent
Good et al.

(10) Patent No.: US 12,150,951 B2
(45) Date of Patent: *Nov. 26, 2024

(54) METHODS FOR PROMOTING ENTRY OF AN AGENT INTO A CELL

(71) Applicant: Tecrea Ltd, London (GB)

(72) Inventors: Liam Good, London (GB); Kantaraja Chindera, London (GB); Valentina Gburcik, London (GB)

(73) Assignee: TECREA LIMITED, London (GB)

( * ) Notice: Subject to any disclaimer, the term of this patent is extended or adjusted under 35 U.S.C. 154(b) by 810 days.

This patent is subject to a terminal disclaimer.

(21) Appl. No.: 16/246,224

(22) Filed: Jan. 11, 2019

(65) Prior Publication Data

US 2019/0142857 A1    May 16, 2019

Related U.S. Application Data

(63) Continuation of application No. 14/348,678, filed as application No. PCT/GB2012/052526 on Oct. 11, 2012, now Pat. No. 10,238,683.

(30) Foreign Application Priority Data

Oct. 11, 2011  (GB) .................................... 1117538

(51) Int. Cl.
*A61K 31/713* (2006.01)
*A61K 9/51* (2006.01)
(Continued)

(52) U.S. Cl.
CPC .......... *A61K 31/713* (2013.01); *A61K 9/5123* (2013.01); *A61K 31/12* (2013.01);
(Continued)

(58) Field of Classification Search
CPC .... A61K 31/713; A61K 47/6929; A61K 9/14; A61K 9/141; A61K 47/62
(Continued)

(56) References Cited

U.S. PATENT DOCUMENTS

| | | | |
|---|---|---|---|
| 4,758,595 A | 7/1988 | Ogenbiyi et al. | |
| 5,958,894 A | 9/1999 | Heath et al. | |

(Continued)

FOREIGN PATENT DOCUMENTS

| WO | WO 2002/022174 | 3/2002 | |
|---|---|---|---|
| WO | WO-2008092928 A2 * | 8/2008 | ........... A61K 31/155 |

(Continued)

OTHER PUBLICATIONS

Allen et al., "Cooperativity in the binding of the cationic biocide polyhexamethylene biguanide to nucleic acids." *Biochemical and Biophysical Research Communications* 318.2 (2004): 397-404.

(Continued)

*Primary Examiner* — James W Rogers
(74) *Attorney, Agent, or Firm* — Parker Highlander PLLC

(57) ABSTRACT

A method for promoting entry of an agent (introduced agent) into a cell, the method comprising the step of complexing the introduced agent in the presence of an entry-promoting agent and then exposing to cells, wherein the entry-promoting agent comprises a linear and/or branched or cyclic polymonoguanide/polyguanidine, polybiguanide, analogue or derivative thereof according to the following Formula 1a & b. The method also provides a means for formation of nanoparticles formed between the entry promoting agent and the introduced agent. wherein: "n", refers to number of repeating units in the polymer, and n can vary from 2 to 1000, for example from 2 or 5 to 10, 20, 30, 40, 50, 60, 70, 80, 90, 100, 150, 200, 250, 300, 350, 400, 450, 500, 600, 700, 800 or 900; $G_1$ and $G_2$ independently represent a cationic group comprising biguanide or guanidine, wherein $L_1$ and $L_2$ are directly joined to a Nitrogen atom of the guanide; $L_1$ and $L_2$ are linking groups between the $G_1$ and $G_2$ cationic groups in the polymer and independently represent an aliphatic group containing $C_1$-$C_{40}$ carbon atoms, for example an alkyl group such as methylene, ethylene, propylene, $C_4$, $C_5$, $C_6$, $C_7$, $C_8$, $C_9$ or $C_{10}$; $C_1$-$C_{10}$, -$C_{20}$, -$C_{30}$, -$C_{40}$, -$C_{50}$-$C_{60}$ -$C_{70}$, -$C_{80}$, -$C_{90}$, -$C_{-100}$, -$C_{110}$, -$C_{120}$, -$C_{130}$ or -$C_{140}$, alkyl; or a $C_1$-$C_{140}$ (for example $C_1$, $C_2$, $C_3$, $C_4$, $C_5$, $C_6$, $C_7$, $C_8$, $C_9$ or $C_{10}$; $C_1$-$C_{10}$, -$C_{20}$, -$C_{30}$, -$C_{40}$, -$C_{50}$ -$C_{60}$, -$C_{70}$, -$C_{80}$, -$C_{90}$, -$C_{100}$, -$C_{110}$, -$C_{120}$, -$C_{130}$ or -$C_{140}$), cycloaliphatic, heterocyclic, aromatic, aryl, alkylaryl, arylalkyl, or oxyalkylene radical; or a polyalkylene radical optionally interrupted by one or more, preferably one, oxygen, nitrogen or sulphur atoms, functional groups or saturated or unsaturated cyclic moiety: N and $G_3$ are optional end groups; X can be either present or absent; $L_3$, $L_4$ and X are linking groups between the $G_4$ and $G_5$ cationic groups in the polymer and independently represent an aliphatic group containing $C_1$-$C_{140}$ carbon atoms, for example an alkyl group such as methylene, ethylene, propylene, $C_4$, $C_5$, $C_6$, $C_7$, $C_8$, $C_9$ or $C_{10}$; $C_1$-$C_{10}$, -$C_{20}$, -$C_{30}$, -$C_{40}$, -$C_{50}$ -$C_{60}$, -$C_{70}$, -$C_{80}$, -$C_{90}$, -$C_{100}$, -$C_{110}$, -$C_{120}$, -$C_{130}$ or -$C_{140}$, alkyl; or $L_3$ and $L_4$ and X can independently be $C_1$-$C_{140}$ (for example $C_1$, $C_2$, $C_3$, $C_4$, $C_5$, $C_6$, $C_7$, $C_8$, $C_9$ or $C_{10}$; $C_1$-$C_{10}$, -$C_{20}$, -$C_{30}$, -$C_{40}$, -$C_{50}$ -$C_{60}$, -$C_{70}$, -$C_{80}$, -$C_{90}$, -$C_{100}$, -$C_{110}$, -$C_{120}$, -$C_{130}$ or -$C_{140}$), cycloaliphatic, heterocyclic, aromatic, aryl, alkylaryl, arylalkyl, oxyalkylene radicals; or a polyalkylene radical optionally interrupted by one or more, preferably one, oxygen, nitrogen or sulphur atoms, functional groups as well as saturated or unsaturated cyclic moiety; "$G_4$" and "$G_5$" are cationic moieties and can be same or different, and at least one of them is a biguanidine moiety or carbamoylguanidine, and the other moiety may be biguanidine or carbamoylguanidine or amine; and cationic moieties $G_4$ and $G_5$ do not contain single guanidine groups. The entry-promoting agent may comprise homogeneous or heterogeneous mixture of one or more of agents arising from formulae 1 a and b, for example polyhexamethylene biguanide (PHMB), polyhex- (Continued)

Figure 1B:
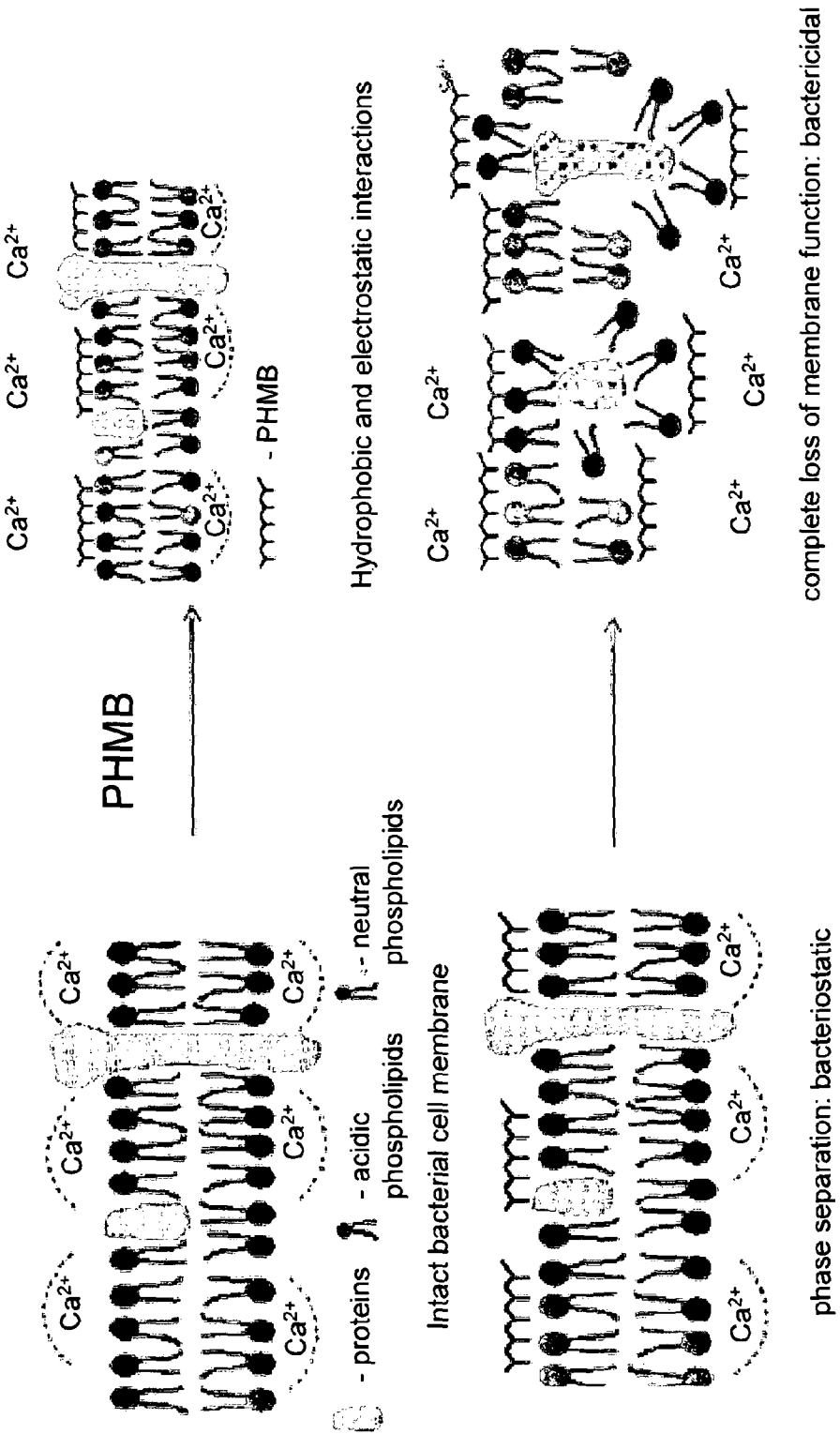

amethylene monoguanide (PHMG), polyethylene biguanide (PEB), polytetramethylene biguanide (PTMB), polyethylene hexamethylene biguanide (PEHMB), polymethylene biguanides (PMB), poly(allylbiguanidnio-co-allylamine), poly(N-vinylbiguanide), polyallybiguanide.

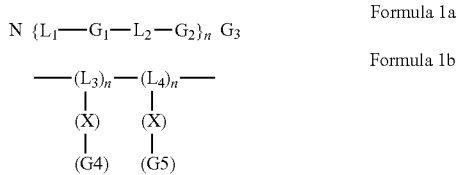

Formula 1a

Formula 1b

12 Claims, 45 Drawing Sheets

(51) Int. Cl.
| | |
|---|---|
| *A61K 31/12* | (2006.01) |
| *A61K 31/496* | (2006.01) |
| *A61K 31/573* | (2006.01) |
| *A61K 47/18* | (2017.01) |
| *A61K 47/54* | (2017.01) |
| *A61K 47/68* | (2017.01) |
| *C12N 15/87* | (2006.01) |
| *A61K 9/14* | (2006.01) |
| *A61K 47/62* | (2017.01) |
| *A61K 47/69* | (2017.01) |
| *B82Y 5/00* | (2011.01) |

(52) U.S. Cl.
CPC .......... *A61K 31/496* (2013.01); *A61K 31/573* (2013.01); *A61K 47/18* (2013.01); *A61K 47/54* (2017.08); *A61K 47/68* (2017.08); *C12N 15/87* (2013.01); *A61K 9/14* (2013.01); *A61K 9/141* (2013.01); *A61K 47/62* (2017.08); *A61K 47/6929* (2017.08); *B82Y 5/00* (2013.01)

(58) Field of Classification Search
IPC ................. A61K 31/713,47/6929, 9/14, 9/141, A61K 47/62
See application file for complete search history.

(56) References Cited

U.S. PATENT DOCUMENTS

| | | | |
|---|---|---|---|
| 7,897,553 | B2 | 3/2011 | Heiler |
| 2004/0009144 | A1 | 1/2004 | Labib |
| 2004/0241206 | A1 | 12/2004 | Ketelson et al. |
| 2007/0104649 | A1 | 5/2007 | Fischer |
| 2008/0242631 | A1 | 10/2008 | Becker |
| 2008/0261841 | A1 | 10/2008 | Heiler |
| 2008/0268051 | A1 | 10/2008 | Hughes |

FOREIGN PATENT DOCUMENTS

| | | |
|---|---|---|
| WO | WO 2009/015143 | 1/2009 |
| WO | WO 2010/086406 | 8/2010 |

OTHER PUBLICATIONS

Allen et al., "The response of *Escherichia coli* to exposure to the biocide poly hexamethylene biguanide." *Microbiology* 152.4 (2006): 989-1000.
Broxton et al., "Injury and recovery of *Escherichia coli* ATCC 8739 from treatment with some poly hexamethylene biguanides." *Microbios* 40.161-162 (1984): 187-193.
Broxton et al., "Interaction of some polyhexamethylene biguanides and membrane phospholipids in *Escherichia coli*." *Journal of Applied Bacteriology* 57.1 (1984): 115-124.
Gilliver, Stephen. "PHMB: a well-tolerated antiseptic with no reported toxic effects." *Journal of Wound Care* (2009).
Hennig et al. "Stimuli-responsive polyguanidino-oxanorbornene membrane transporters as multicomponent sensors in complex matrices." *Journal of the American Chemical Society* 130.31 (2008): 10338-10344.
http://merriam-webster.com/dictionary/analogue retrieved on Mar. 31, 2017.
http://merriamwebster.com/dictionary/derivative retrieved on Dec. 9, 2015.
Ikeda et al., "Interaction of a polymeric biguanide biocide with phospholipid membranes." *Biochimica et Biophysica Acta (BBA)-Biomembranes* 769.1 (1984): 57-66.
Kolonko et al., "A polymeric domain that promotes cellular internalization", *Journal of the American Chemical Society*, 130(17):5626-5627, 2008.
Lucas et al., Analysis of polyhexamethylene biguanide in multipurpose contact lens solutions:, *Talanta*, 80: 1016-1019, 2009.
Montague, "Reregistration Eligibility Decision (RED) for PHMB", *United States Environmental Protection Agency*, 2004.
Muller and Kramer, "Biocompatibility index of antiseptic agents by parallel assessment of antimicrobial activity and cellular cytotoxicity", *J Antimicrobial Chemotherapy*, 61: 1281-1287, 2008.
Office Communication issued in U.S. Appl. No. 14/348,678, dated Apr. 14, 2016.
Office Communication issued in U.S. Appl. No. 14/348,678, dated Aug. 30, 2016.
Office Communication issued in U.S. Appl. No. 14/348,678, dated Apr. 11, 2017.
Office Communication issued in U.S. Appl. No. 14/348,678, dated Aug. 15, 2017.
Office Communication issued in U.S. Appl. No. 14/348,678, dated Dec. 13, 2017.
PCT International Preliminary Report on Patentability issued in International Application No. PCT/GB2012/052526, mailed Apr. 24, 2014.
PCT International Search Report and Written Opinion issued in International Application No. PCT/GB2012/052526, mailed Feb. 21, 2013.
Schnuch et al., "The biocide polyhexamethylene biguanide remains an uncommon contact allergen", *Contact Dermatitis*, 56: 235-239 , 2007.
Wender et al. "The design of guanidinium-rich transporters and their internalization mechanisms." *Advanced Drug Delivery Reviews* 60.4-5 (2008): 452-472.
Zhou et al., "Novel binding and efficient cellular uptake of guanidine-based peptide nucleric acids (GPNA)", *Journal of the American Chemical Society*, 125(23):6878-6879, 2003.
Yu, Jia-Hui, et al. "Guanidinylated poly (allyl amine) as a gene carrier." *Journal of Applied Polymer Science* 112.2 (2009): 926-933.
Barrett, "Consensus Document", dated Jan. 6, 2010, retrieved from www.wounds-uk.com/pdf/content_9484.pdf on Nov. 28, 2016.
Extended European Search Report issued in European Application No. 21150737.1, dated May 7, 2021.
Gray, David, et al. "PHMB and its potential contribution to wound management." *Wounds UK* 6.2 (2010): 40-46.

\* cited by examiner

Figure 1a

- Polyhexametheylene biguandie (PHMB) is a cationic polymer with broad spectrum antimicrobial agent and less toxic to mammalian cells (Vantocol™ Arch biocides Limited, UK)

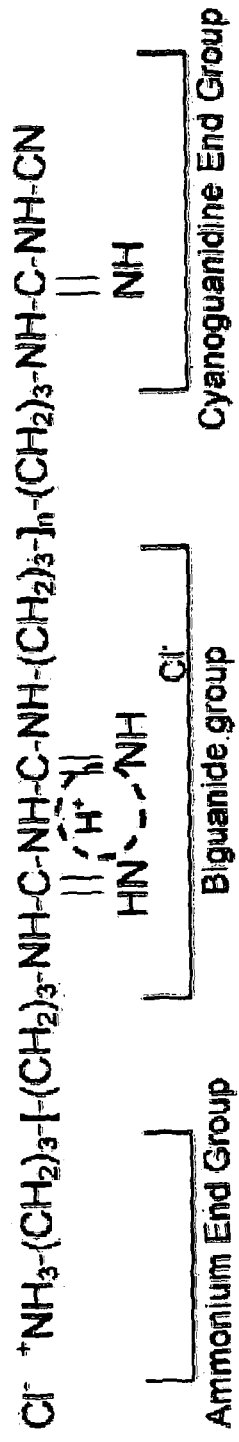

- n = 2 to 40, average n:11, average molecular weight: 3025

- End groups: amine, guanidine and cyanoguanidine

Polyhexametheylene monoguande (PHMG) is an analogue of PHMB with antimicrobial properties

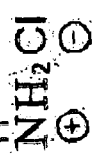

(Zhou et al. 2010)

Purpose: to assess whether free PHMB can enter cells?

Figure 9

HeLa, HEK, THP-1 monocytes and macrophages, J774 macrophage cells were subcultured into 24 well tissue culture plates a day before experiment

→

Cells at 60% confluence were treated with PHMB-FITC in DEM and incubated for 2hr

→

After 2hr cells were washed 3x with PBS and observed under fluorescence microscope Gel shift assay to show interaction of PHMB with oligonucleotide Changes in the fluorescence of FAM-Oligonucleotide upon interaction with PHMB

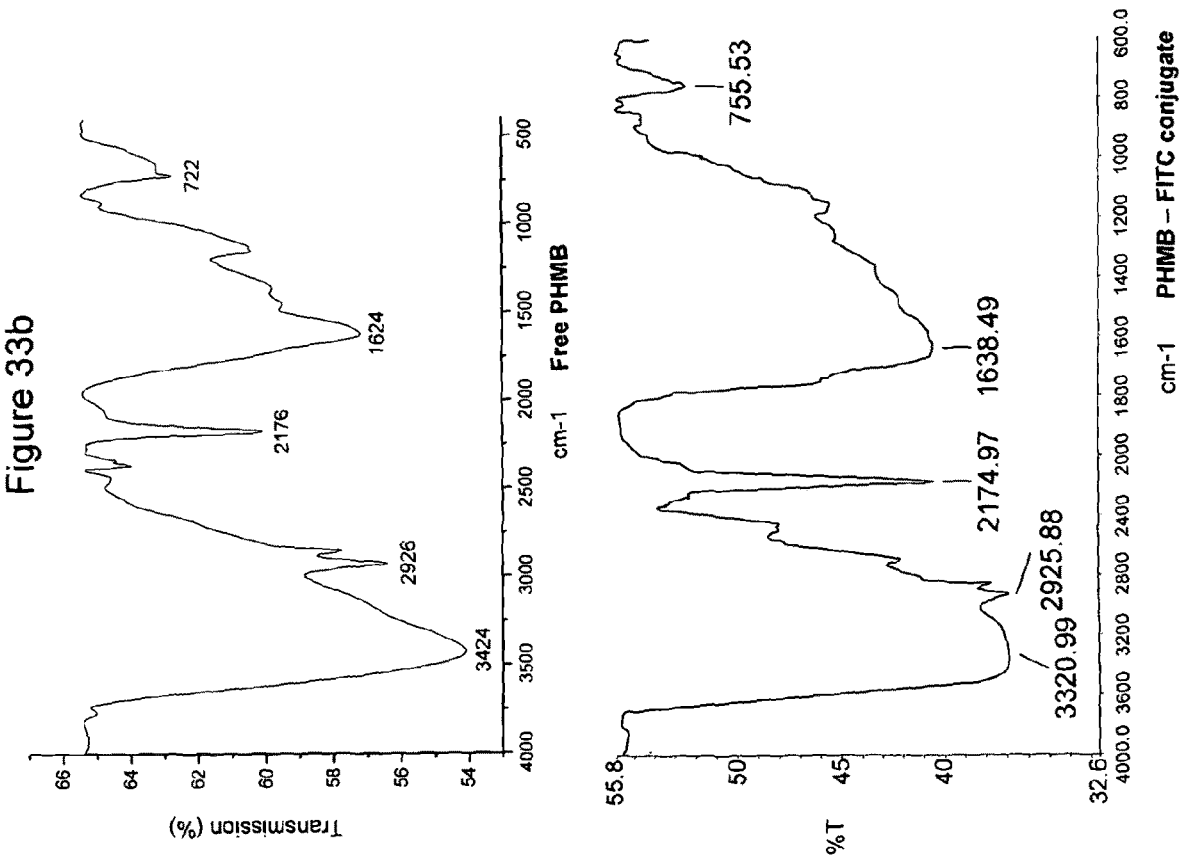

PHMB forms nanoparticles with a wide variety of cargo molecules

HeLa cells transfected with 3 µg branched PHMB and 1 µg pEGFP complex, showing expression of GFP after 36 hours.

HeLa cells transfected with 3 µg branched PHMG and 1 µg pEGFP complex, showing expression of GFP after 36 hours.

METHODS FOR PROMOTING ENTRY OF AN AGENT INTO A CELL

This application is a continuation of U.S. application Ser. No. 14/348,678, filed Mar. 31, 2014, as a national phase application under 35 U.S.C. § 371 of International Application No. PCT/GB2012/052526, filed Oct. 11, 2012, which claims priority to United Kingdom Application No. 1117538.7, filed Oct. 11, 2011. The entire text of each of the above referenced disclosures is specifically incorporated herein by reference.

The present invention relates to the field of methods and reagents for promoting entry of an agent, for example a nucleic acid, into a cell.

Nucleic acids and analogues thereof have many applications in basic research and both prophylactic and therapeutic interventions. However, prokaryotic and eukaryotic cells are in general impermeable to nucleic acids/analogues. Typically nucleic acid/analogue uptake has required delivery vehicles, either viral or non-viral, in order to reach their potential. To be effective, the delivery vehicle/nucleic acid or analogue combination or complex must overcome many challenges, for example extracellular degradation, cell membrane barrier penetration and intracellular release, whilst minimising cytotoxicity and antigenicity. Many polypeptides (for example proteins, peptides) and other bioactive molecules also are cell impermeable, but otherwise useful. For example the activity of many compounds in biochemical assays is much higher than in cellular assays or in vivo. The drop off in cellular activity is believed to be largely due to poor delivery into cells.

Lipofectamine is a widely used example of an agent used in promoting entry of agents, for example nucleic acids, into cells. However, lipofectamine is considered to have toxic effects on mammalian cells in particular, which can, for example, make in vitro experiments difficult to assess and in vivo experiments difficult to perform.

Other proposed entry-promoting agents are described in, for example, WO 2009/015143 (Biodegradable cationic polymer gene transfer compositions and methods of use); WO 02/22174 (cationic lipopolymer as biocompatible gene delivery agent); WO2010/086406 (non-viral transfection agent); U.S. Pat. No. 5,958,894 (amphiphilic biguanide derivatives).

There is a need for alternative entry-promoting agents, for example for nucleic acids and other substances where activities are limited by poor cell entry. The present invention identifies entry-promoting agents and methods. Such entry-promoting agents and methods are considered to be beneficial, for example in providing good entry promotion, poor antigenicity, low cost and/or low toxicity, for example particularly for eukaryotic cells. Such entry-promoting agents and methods may, for example, be useful in areas such as nucleic acid/analogue transfection, for example functional studies; generation of stable cell lines; gene silencing; and DNA vaccination. For example, such entry-promoting agents and methods may, for example, be useful in relation to RNA interference (RNAi) or other antisense technologies, as will readily be appreciated by those skilled in the art. The challenge of delivery of reagents or drugs into cells is not limited to only nucleic acids. Proteins and peptides also enter cells very poorly in general and entry-promoting technology would be useful. Also, many molecules that are described as "small molecules" being less than 1000 grams/mol enter cells poorly and their usefulness as reagents or drugs would be enhance by improved cell delivery technology.

PHMB (polyhexamethylene biguanide) is known as a safe and effective biocidal agent and is used as a sanitiser and preservative: U.S. Pat. Nos. 7,897,553, 4,758,595, US2008261841; US 20040009144. The present inventors have surprisingly found that PHMB and related molecules are useful entry-promoting agents. It was surprisingly observed that PHMB (for example) itself enters a wide range of cells, including bacteria, fungi and mammalian cells. More surprisingly, PHMB (for example) is able to form nanoparticles with a wide range of molecules and deliver these molecules into such cells. Finally the delivered molecules ranging from nucleic acids to small molecules were found to be functional inside cells.

The listing or discussion of an apparently prior-published document in this specification should not necessarily be taken as an acknowledgement that the document is part of the state of the art or is common general knowledge.

A first aspect of the invention provides a method for promoting entry of an agent into a cell, the method comprising the step of exposing the cell to the introduced agent in the presence of a polymer, wherein the polymer comprises a linear and/or branched polymonoguanide/polyguanidine, polybiguanide, analogue or derivative thereof, for example according to the following formula 1a or formula 1b, with examples given in tables 1 and 2, below:

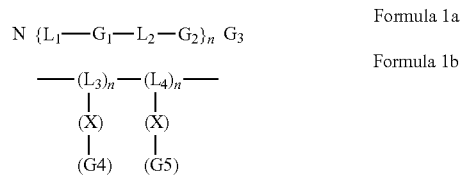

Formula 1a

Formula 1b wherein:

"n", refers to number of repeating units in the polymer, and n can vary from 2 to 1000, for example from 2 or 5 to 10, 20, 30, 40, 50, 60, 70, 80, 90, 100, 150, 200, 250, 300, 350, 400, 450, 500, 600, 700, 800 or 900;

$G_1$ and $G_2$ independently represent a cationic group comprising biguanide or guanidine, wherein $L_1$ and $L_2$ are directly joined to a Nitrogen atom of the guanide. Thus, the biguanide or guanidine groups are integral to the polymer backbone. The biguanide or guanidine groups are not side chain moieties in formula 1a.

Example of Cationic Groups:

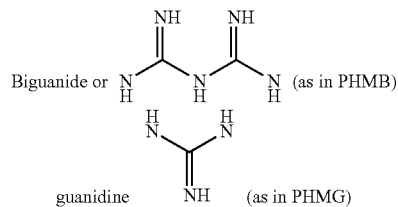

In the present invention, $L_1$ and $L_2$ are the linking groups between the $G_1$ and $G_2$ cationic groups in the polymer. $L_1$ and $L_2$ can independently represent an aliphatic group containing $C_1$-$C_{140}$ carbon atoms, for example an alkyl group such as methylene, ethylene, propylene, $C_4$, $C_5$, $C_6$, $C_7$, $C_8$, $C_9$ or $C_{10}$; $C_1$-$C_{10}$, -$C_{20}$, -$C_{30}$, -$C_{40}$, -$C_{50}$ -$C_{60}$, -$C_{70}$, -$C_{80}$, -$C_{90}$, -$C_{100}$, -$C_{110}$, -$C_{120}$, -$C_{130}$ or -$C_{140}$, alkyl; or $L_1$ and $L_2$ can (independently) be $C_1$-$C_{140}$ (for example $C_1$, $C_2$, $C_3$, $C_4$, $C_5$, $C_6$, $C_7$, $C_8$, $C_9$ or $C_{10}$; $C_1$-$C_{10}$, -$C_{20}$, -$C_{30}$, -$C_{40}$, -$C_{50}$ -$C_{60}$, -$C_{70}$, -$C_{80}$, -$C_{90}$, -$C_{100}$, -$C_{110}$, -$C_{120}$, -$C_{130}$ or -$C_{140}$), cycloaliphatic, heterocyclic, aromatic, aryl, alkylaryl, arylalkyl, oxyalkylene radicals, or $L_1$ and $L_2$ can (independently) be a polyalkylene radical optionally interrupted by one or more, preferably one, oxygen, nitrogen or sulphur atoms, functional groups as well as saturated or unsaturated cyclic moiety. Examples of suitable $L_1$ and $L_2$ are groups are listed in table 1.

$L_1$, $L_2$, $G_1$ and $G_2$ may have been modified using aliphatic, cycloaliphatic, heterocyclic, aryl, alkaryl, and oxyalkylene radicals.

N and $G_3$ are preferably end groups. Typically the polymers of use in the invention have terminal amino (N) and cyanoguanidine ($G_3$) or guanidine ($G_3$) end groups. Such end groups may be modified (for example with 1,6-diaminohexane, 1,6 di(cyanoguanidino)hexane, 1,6-diguanidinohexane, 4-guanidinobutyric acid) by linkage to aliphatic, cycloaliphatic heterocyclic, heterocyclic, aryl, alkylaryl, arylalkyl, oxyalkylene radicals. In addition, end groups may be modified by linkage to receptor ligands, dextrans, cyclodextrins, fatty acids or fatty acid derivatives, cholesterol or cholesterol derivatives or polyethylene glycol (PEG). Optionally, the polymer can end with guanidine or biguanide or cyanoamine or amine or cyanoguanidine at N and $G_3$ positions or cyanoamine at N and cyanoguanidine at $G_3$ position or guanidine at N and Cyanoguanidne at $G_3$ positions or L1 amine at G3 and cyanoguanidine at N. G3 can be $L_1$-amine, $L_2$-cyanoguanidine or $L_2$-guanidine. Depending on the number of polymerization (n) or polymer chain breakage and side reactions during synthesis, heterogeneous mixture of end groups can arise as described above as an example. Thus, the N and G3 groups can be interchanged/present as a heterogeneous mixture, as noted above. Alternatively N and $G_3$ may be absent and the polymer may be cyclic, in which case the respective terminal $L_1$ and $G_2$ groups are linked directly to one another.

In formula 1b, X can be either present or absent. $L_3$, $L_4$ and X are as noted above for "$L_1$ or $L_2$". In Thus, $L_3$ and $L_4$ and X are the linking groups between the $G_4$ and $G_5$ cationic groups in the polymer. $L_3$ and $L_4$ and X can independently represent an aliphatic group containing $C_1$-$C_{140}$ carbon atoms, for example an alkyl group such as methylene, ethylene, propylene, $C_4$, $C_5$, $C_6$, $C_7$, $C_8$, $C_9$ or $C_{10}$; $C_1$-$C_{10}$, -$C_{20}$, -$C_{30}$, -$C_{40}$, -$C_{50}$, -$C_{60}$, -$C_{70}$, -$C_{80}$, -$C_{90}$, -$C_{100}$, -$C_{110}$, -$C_{120}$, -$C_{130}$ or -$C_{140}$, alkyl; or $L_3$ and $L_4$ and X can independently be $C_1$-$C_{140}$ (for example $C_1$, $C_2$, $C_3$, $C_4$, $C_5$, $C_6$, $C_7$, $C_8$, $C_9$ or $C_{10}$; $C_1$-$C_{10}$, -$C_{20}$, -$C_{30}$, -$C_{40}$, -$C_{50}$, -$C_{60}$, -$C_{70}$, -$C_{80}$, -$C_{90}$, -$C_{100}$, -$C_{110}$, -$C_{120}$, -$C_{130}$ or -$C_{140}$), cycloaliphatic, heterocyclic, aromatic, aryl, alkylaryl, arylalkyl, oxyalkylene radicals, or $L_3$ and $L_4$ and X can independently be a polyalkylene radical optionally interrupted by one or more, preferably one, oxygen, nitrogen or sulphur atoms, functional groups as well as saturated or unsaturated cyclic moiety. Examples of suitable $L_3$ and $L_4$ and X are groups are listed in table 2.

"$G_4$" and "$G_5$" are cationic moieties and can be same or different. At least one of them is a biguanidine moiety or carbamoylguanidine, and the other moiety may be as above (biguanidine or carbamoylguanidine) or amine. For the avoidance of doubt, in formula 1b, cationic moiety $G_4$ and $G_5$ do not contain only single guanidine groups. For example, $G_4$ and $G_5$ typically do not contain single guanidine groups. Examples of such compounds are polyallylbiguanide, poly(allylbiguanidnio-co-allylamine), poly(allylcarbamoylguanidino-co-allylamine), polyvinylbiguanide, as listed in table 2.

Example of polyallylbiguanide is as shown below

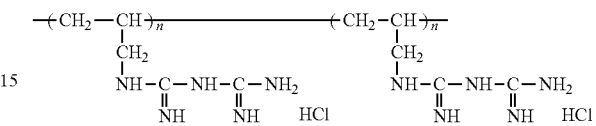

In case of polyallylbigunidine $L_3$ and $L_4$ are identical, $G_4$ and G5 are similar, thus polyallylbiguanide can be simplified as below.

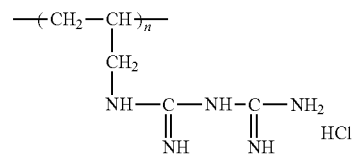

Example of poly(allylcarbamoylguanidnio-co-allylamine) is as shown below

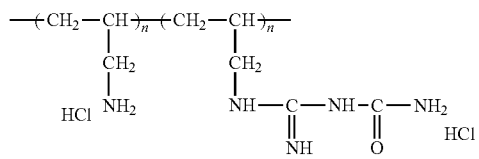

The polymers for use in the invention will generally have counter ions associated with them. Suitable counter ions include but are not limited to the following: halide (for example chloride), phosphate, lactate, phosphonate, sulfonate, amino carboxylate, carboxylate, hydroxy carboxylate, organophosphate, organophosphonate, organosulfornate and organosuflate.

Polymers for use in the invention can be either heterogeneous mixtures of polymers of different "n" number or homogenous fractions comprising specified "n" numbers purified by standard purification methods. As indicated above the polymers may also be cyclic and in addition may be branched.

Preferred numbers for "n" include 2-250, 2-100, 2-80 and 2-50.

TABLE 1

Examples of polymer analogues arising from formula 1a.

| Name | $L_1$ | $G_1$ | $L_2$ | $G_2$ |
| --- | --- | --- | --- | --- |
| Polyhexamethylene biguanide (PHMB) | $(CH_2)_6$ | Biguanide | $(CH_2)_6$ | Biguanide |
| Polyethylene biguanide (PEB) | $(CH_2)_2$ | Biguanide | $(CH_2)_2$ | Biguanide |
| Polyethylenetetramethylene biguanide | $(CH_2)_2$ | Biguanide | $(CH_2)_4$ | Biguanide |

TABLE 1-continued

Examples of polymer analogues arising from formula 1a.

| | | | | |
|---|---|---|---|---|
| Polyethylene hexamethylene biguanide (PEHMB) | $(CH_2)_2$ | Biguanide | $(CH_2)_6$ | Biguanide |
| Polypropylene biguanide, Polyaminopropyl biguanide (PAPB) | $(CH_2)_3$ | Biguanide | $(CH_2)_3$ | Biguanide |
| Poly-[2-(2-ethoxy)-ethoxyethyl]-biguanide-chloride] (PEEG) | $(CH_2CH_2OCH_2CH_2OCH_2CH_2)$ | Biguanide | $(CH_2CH_2OCH_2CH_2OCH_2CH_2)$ | Biguanide |
| Polypropylenehexamethylene biguanide | $(CH_2)_3$ | Biguanide | $(CH_2)_6$ | Biguanide |
| Polyethyleneoctamethylene biguanide | $(CH_2)_2$ | Biguanide | $(CH_2)_8$ | Biguanide |
| Polyethylenedecamethylene biguanide | $(CH_2)_2$ | Biguanide | $(CH_2)_{10}$ | Biguanide |
| Polyethylenedodecamethylene biguanide | $(CH_2)_2$ | Biguanide | $(CH_2)_{12}$ | Biguanide |
| Polytetramethylenehexamethylene biguanide | $(CH_2)_4$ | Biguanide | $(CH_2)_6$ | Biguanide |
| Polytetramethylenebiguanide | $(CH_2)_4$ | Biguanide | $(CH_2)_4$ | Biguanide |
| Polypropyleneoctamethylene biguanide | $(CH_2)_3$ | Biguanide | $(CH_2)_8$ | Biguanide |
| Polytetramethyleneoctamethylene Biguanide | $(CH_2)_4$ | Biguanide | $(CH_2)_8$ | Biguanide |
| Polyhexamethylene diethylenetriamine biguanide | $(CH_2)_6$ | Biguanide | $CH_2-CH_2-NH-CH_2-CH_2$ | Biguanide |
| Polyhexamethylene guanide (PHMG) | $(CH_2)_6$ | guanidine | $(CH_2)_6$ | guanidine |
| Polyethylene guanide | $(CH_2)_2$ | guanidine | $(CH_2)_2$ | guanidine |
| Polyethylenetetramethylene guanide | $(CH_2)_2$ | guanidine | $(CH_2)_4$ | guanidine |
| Polyethylene hexamethylene guanide | $(CH_2)_2$ | guanidine | $(CH_2)_6$ | guanidine |
| Polypropylene guanide, Polyaminopropyl guanide (PAPB) | $(CH_2)_3$ | guanidine | $(CH_2)_3$ | guanidine |
| Poly-[2-(2-ethoxy)-ethoxyethyl]-guanide | $(CH_2CH_2OCH_2CH_2OCH_2CH_2)$ | guanidine | $(CH_2CH_2OCH_2CH_2OCH_2CH_2)$ | guanidine |
| Polypropylenehexamethylene guanide | $(CH_2)_3$ | guanidine | $(CH_2)_6$ | guanidine |
| Polyethyleneoctamethylene guanide | $(CH_2)_2$ | guanidine | $(CH_2)_8$ | guanidine |
| Polyethylenedecamethylene guanide | $(CH_2)_2$ | guanidine | $(CH_2)_{10}$ | guanidine |
| Polyethylenedodecamethylene guanide | $(CH_2)_2$ | guanidine | $(CH_2)_{12}$ | guanidine |
| Polytetramethylenehexamethylene guanide | $(CH_2)_4$ | guanidine | $(CH_2)_6$ | guanidine |
| Polypropyleneoctamethylene guanide | $(CH_2)_3$ | guanidine | $(CH_2)_8$ | guanidine |
| Polytetramethylene guanide | $(CH_2)_4$ | guanidine | $(CH_2)_4$ | guanidine |
| Polyhexamethylene diethylenetriamine guanide | $(CH_2)_6$ | guanidine | $CH_2-CH_2-NH-CH_2-CH_2$ | guanidine |

CAS numbers for example compounds arising from formula 1a

| Polymer | CAS Number |
|---|---|
| Polyhexamethylene biguanide hydrochloride (PHMB) | 27083-27-8 |
| | 32289-58-0 |
| Polyhexamethylene guanidine hydrochloride (PHMG) | 57028-96-3 |
| Poly-[2-(2-ethoxy)-ethoxyethyl]-guanidinium-chloride] (PEEG) | 374572-91-5 |

TABLE 2

Examples of polymer analogues arising from formula 1b.

| Name | $L_3$ | $G_4$ | $L_4$ | $G_5$ | x |
|---|---|---|---|---|---|
| Polyallylbiguanide | $(CH_2-CH)$ | Biguanide | $(CH_2-CH)$ | Biguanide | $CH_2$ |
| poly(allylbiguanidnio-co-allylamine) | $(CH_2-CH)$ | amine | $(CH_2-CH)$ | biguanide | $CH_2$ |
| poly(allylcarbamoylguanidino-co-allylamine) | $(CH_2-CH)$ | amine | $(CH_2-CH)$ | Carbamoyl guanidine | $CH_2$ |
| polyvinylbiguanide | $(CH_2-CH)$ | Biguanide | $(CH_2-CH)$ | biguanide | absent |

The entry-promoting agent used in the method of the invention may comprise linear, branched or dendrimeric molecules. The entry promoting agent may comprise a combination of linear, branched or dendrimeric molecules. The entry promoting agent may comprise one or any combination of molecules of Formula 1a or formula 1b, for example as described above.

For example, the entry-promoting agent can comprise one or more of polyhexamethylene biguanide (PHMB), polyhexamethylene monoguanide (PHMG), polyethylene biguanide (PEB), polytetramethylene biguanide (PTMB) or polyethylene hexamethylene biguanide (PEHMB). Some examples are listed in table 1 and 2.

Thus, the entry-promoting agent may comprise homogeneous or heterogeneous mixtures of one or more of polyhexamethylene biguanide (PHMB), polyhexamethylene monoguanide (PHMG), polyethylene biguanide (PEB), polytetramethylene biguanide (PTMB), polyethylene hexamethylene biguanide (PEHMB), polymethylene biguanides (PMB), poly(allylbiguanidnio-co-allylamine), poly(N-vinylbiguanide), polyallybiguanide The compounds can be synthesised in the laboratory by standard procedures or may be obtained from commercial suppliers, as will be well known to those skilled in the art.

PHMB, for example, may also have synonyms poly (hexamethylene)biguanide hydrochloride; polymeric biguanide hydrochloride; polyhexanide; biguanide; CAS Number 27083-27-8; 32289-58-0; IUPAC name Poly(iminoimidocarbonyl)iminohexamethylene hydrochloride. PHMB can be synthesised in the laboratory by standard procedures or may be obtained from suppliers, for example, Arch (archchemicals.com/Fed/BIO/Products/phmb.htm). Typically $n=2$ to 40, average n:11, average molecular weight: 3025. PHMB is sold as a biocide, for example for use in hygiene products, swimming pool water treatment and wound dressings.

Polyhexamethylene monoguanide (PHMG) can be synthesised in the laboratory by standard procedures or obtained from suppliers, for example from Shanghai Scunder Industry Co., Ltd, scunder.en.busytrade.com/products/info/683633/PHMG.html As will be appreciated by those skilled in the art, the entry-promoting polymer may be a copolymer or heteropolymer ie the monomers may not be intended to be identical. However, typically the monomer units may be intended to be identical.

The entry promoting polymer in the present invention can be used for delivery into both prokaryotic and eukaryotic cells. Thus, the cell may be a prokaryotic cell. Examples of such cells will be well known to those skilled in the art and include Gram negative bacteria; Gram positive bacteria; and mycobacteria or acid fast bacteria, for example *Mycobacterium smegmatis*. Examples of Gram-negative bacteria include *E. coli, S. enterica*, for example *S. entericia* serovar *Typhimurium, Salmonella* spp and *Campylobacter* spp. Examples of Gram-positive bacteria include *S. aureus*.

The cell may alternatively be a eukaryotic cell, for example a fungal cell, for example *Aspergillus*, for example *A. fumigatus; Candida* spp; *Saccharomyces* spp; *Pichia* spp. The cell may be a mammalian cell (which may be a cell in cell culture, or a cell present in a tissue or organ). The cell may, for example, be a human, mouse, rat, rabbit, bovine or dog (or, for example, any other wild, livestock/domesticated animal) cell. The cell may, for example, be a stable cell line cell, or a primary cell, adherent or suspension cell. As examples, the cell may be a macrophage, osteosarcoma or HeLa cell line cell or a mouse primary cell.

The eukaryotic cell may alternatively be a plant cell (for example a monocotyledonous or dicotyledenous plant cell; typically an experimental, crop and/or ornamental plant cell, for example *Arabidopsis*, maize); fish (for example Zebra fish; salmon), bird (for example chicken or other domesticated bird), insect (for example *Drosophila*; bees), Nematoidia or Protista (for example *Plasmodium* spp or *Acantamoeba* spp) cell.

The introduced agent may typically be or comprise a bioactive compound, for example a pharmaceutically active substance, or a diagnostic/imaging tool or probe, typically that has poor cell uptake properties. The introduced agent may comprise a nucleic acid or nucleic acid analogue. The nucleic acid or nucleic acid analogue may, for example, be or comprise DNA or RNA or both. The nucleic acid or nucleic acid analogue may typically be an antisense nucleobase oligomer, or a sense nucleobase oligomer (for example encoding a polypeptide or a structural or regulatory nucleic acid). The nucleobase oligomer may be any type of nucleic acid analogue or mimic that retains the capacity for base pairing, as will be well known to those skilled in the art. For example, the nucleic acid/analogue or nucleobase oligomer may be a phosphorothioate, 2'O-methyl nucleic acid, locked nucleic acid, peptide nucleic acid (PNA) oligomer. Alternatively, the nucleic acid/analogue or nucleobase oligomer may be, for example, a phosphorothioate, morpholino oligomer (PMO). The skilled person will readily be able to determine whether a given nucleobase oligomer chemistry is compatible with the nucleobase oligomer retaining the ability to bind specifically to a target nucleic acid, for example to act as a probe, guide polypeptide/nucleic acid expression, or mediate gene silencing (for example through antisense or RNAi, as will be well known to those skilled in the art). The skilled person will also readily be able to determine whether a given nucleobase oligomer chemistry is compatible with promotion of entry by the entry-promoting agent: it is considered that an entry-promoting agent as set out above is useful generally with nucleic acids/analogues/nucleobase oligomers.

PNA and morpholino oligomers typically have uncharged (rather than anionic) backbones. There has previously been very modest success in PNA delivery. Many strategies that work with DNA and RNA do not work with PNA and morpholino oligomers, which are typically uncharged. We have surprisingly found that the entry-promoting agent of the present invention works with such molecules.

The nucleic acid/analogue/nucleobase oligomer may be single stranded or double stranded. The nucleobase oligomer may be able to act as a probe, in guiding polypeptide/nucleic acid expression, or as an RNAi molecule, for example small interfering RNA (siRNA) or microRNA, as an aptamer or ligand as is well known to those skilled in the art. Typically the nucleic acid/analogue/nucleobase oligomer may be single stranded, particularly when the cell is prokaryotic. When the cell is eukaryotic (for example when the cell is a yeast or other fungus, or is a mammalian cell), the nucleobase oligomer may typically be single stranded or double stranded, which may include a mixture of single and double stranded regions.

The nucleobase oligomer can be any molecule that hybridizes by a sequence specific base pairing to a complementary DNA and/or RNA sequence. In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds.

Further relevant features of nucleobase oligomers, for example antisense nucleobase oligomers, will be well known to those skilled in the art, and are, for example, set out in WO 02/079467 (hereby incorporated by reference), for example on page 2, lines 1 to 34 (antisense RNA regulation; PNA preparation, use as an antisense compound; cell uptake); page 6, lines 14 to 34 (hybridization to target sequence); page 8, lines 1 to 25 (types of nucleobase oligomer); page 8, line 27 to page 14, line 2 (length of antisense compounds; types of more on types of nucleobase oligomer); page 14, line 19 to page 15, line 19 (cell uptake; length considerations); page 15, line 29 to page 16, line 26 (cell uptake); page 16, line 28 to page 17, line 6 (synthesis); page 18, line 33 to page 19, line 6 (linker connection between PNA and peptide).

The nucleobase oligomer may comprise, for example, phosphorothioate, 2'O-methyl, 2'Fluoro, locked nucleic acid (LNA), morpholino, PNA or deoxy nucleotides.

See, for example:

Phosphorothioate ncbi.nlm.nih.gov/pubmed/1772569
LNA pnas.org/content/97/10/5633.short
PNA ncbi.nlm.nih.gov/pubmed?term=Progress%20in%20-Developing%20PNA%20as%20a%20Gene-Targeted%20Drug
morpholino liebertonline.com/doi/abs/10.1089/oli.1.1997.7.187

The introduced agent may comprise plasmid or other vector DNA (which may be modified DNA), as will be well known to those skilled in the art. Typically plasmid or vector DNA may encode and/or be suitable for expressing (or promoting expression of, for example by encoding a cellular factor which, when expressed, activates the expression of an endogenous gene) a polypeptide or nucleic acid of interest. Alternatively, the introduced agent may comprise an RNA (which may be modified RNA, for example as discussed above) molecule, for example the introduced agent may comprise an siRNA molecule ie a molecule capable of mediating RNA interference, as well known to those skilled in the art.

Successfully transformed or transfected cells, ie. cells that contain a DNA construct as noted above, can be identified by well known techniques. For example, one selection technique involves incorporating into the expression vector a DNA sequence (marker) that codes for a selectable trait in the transformed cell. These markers include dihydrofolate reductase, G418 or neomycin resistance for eukaryotic cell culture, and tetracycline, kanamycin or ampicillin resistance genes for culturing in E. coli and other bacteria. Alternatively, the gene for such selectable trait can be on another vector, which is used to co-transform the desired host cell.

The marker gene can be used to identify transformants but it is desirable to determine which of the cells contain recombinant DNA molecules and which contain self-ligated vector molecules. This can be achieved by using a cloning vector where insertion of a DNA fragment destroys the integrity of one of the genes present on the molecule. Recombinants can therefore be identified because of loss of function of that gene.

Successfully transformed cells, ie cells that contain a DNA construct as noted above, can be identified by well known techniques. For example, another method of identifying successfully transformed cells involves growing the cells resulting from the introduction of an expression construct as noted above can be grown to produce the encoded polypeptide. Cells can be harvested and lysed and their DNA content examined for the presence of the DNA using a method such as that described by Southern (1975) J. Mol. Biol. 98, 503 or Berent et al (1985) Biotech. 3, 208. Alternatively, the presence of the protein in the supernatant can be detected using antibodies as well known to those skilled in the art.

In addition to directly assaying for the presence of recombinant DNA, successful transformation can be confirmed by well known phenotypic assays, for example immunological methods, when the recombinant DNA is capable of directing the expression of the protein. For example, cells successfully transformed or transfected with an expression vector produce proteins displaying appropriate antigenicity. Samples of cells suspected of being transformed or transfected are harvested and assayed for the protein using suitable antibodies.

Methods for determining whether an antisense reagent has been taken up by a cell will also be well known to those skilled in the art, for example methods similar in concept to those described above; the introduced antisense agent may result in a reduction in endogenous gene function or expression.

The introduced agent may comprise a polypeptide (by which term is included smaller polypeptides or fragments of larger polypeptides, which may be termed peptides, for example of fewer than 50 amino acids in length, typically 10-20 amino acid residues in length; as well as larger or full length polypeptides which may be termed proteins, for example of more than 50 amino acids in length). http://en.wikipedia.org/wiki/Peptide. The term polypeptide is intended to encompass peptidomimetic compounds, as will be well known to those skilled in the art. One example of peptidomimetic compounds is discussed in Sherman and Spatola, J. Am. Chem. Soc., 112: 433 (1990). The polypeptide may be a therapeutic polypeptide, for example a polypeptide that replaces the function of a missing/depleted and/or defective polypeptide; or may be an antigenic polypeptide, for example a polypeptide intended to serve as a vaccine, or may act as a ligand that binds to another protein or peptide. For example, the polypeptide may be an agonist or antagonist of a cellular protein. The delivered peptide or protein may act by either inhibiting or promoting an enzyme's function in a cell to build understanding of the role of the enzyme in a cell or to have a therapeutic or other useful effect in the cell, or in the tissue, organ or body of which the cell may be a part.

Methods for determining whether a polypeptide has been taken up by a cell will also be well known to those skilled in the art. For example the protein may have fluorescence properties, such as green fluorescence protein (GFP) that can be observed and monitored using fluorescence microscopy, flow cytometry or similar methods. Also, uptake may be assessed using antibody-mediated staining. Finally, diverse functional studies can be utilized, according to the known function of the protein. For example, if the protein is a transcription factor, genes regulated by the factor could be profiled to assess changes in expression levels. Alternatively, the protein may be a kinase, and changes in phosphorylation of its known substrates could be measured using phosphorylation assays. Methods for determining whether a peptide has been taken up by a cell will also be well known to those skilled in the art. For example the peptide may be fluorescently labelled, using for example fluorescein, which can be observed and monitored using fluorescence microscopy, flow cytometry or similar methods. Also, uptake may be assessed using antibody-mediated staining. Finally, diverse functional studies can be utilized, according to the known function(s) of proteins and peptides. Alternatively, if the peptide is a ligand, the downstream effects of peptide interaction with a receptor could be assessed. If the protein/peptide is a toxin, the toxic effects could be assayed. Finally many peptides and proteins are immunogenic and the immune function effects following delivery can be assessed using methods that are well known to molecular and cellular immunologists and others skilled in the art.

The introduced agent may comprise a small drug or bioactive reagent, for example having a molecular weight of less than 1000 or 2000 Da. The small drug or bioactive reagent may have poor cell uptake or stability properties in the absence of the entry-promoting agent of the present invention. An example is gentamycin, which is a useful antibiotic, but does not readily enter host cells. A second example is amphotericin B. Negatively charged or highly hydrophobic molecules may be introduced agents that may benefit from the delivery technology of the present invention.

Methods for determining whether a small molecule has been taken up by a cell will also be well known to those skilled in the art. The small molecule may have inherent fluorescent properties allowing uptake to be monitored using the methods described about. Also, radioisotopes can be incorporated, or small fluorophores may be conjugated providing fluorescent properties. For example a DNA ligand small molecule that increases in fluorescence upon binding to DNA provides a convenient assay for delivery, showing both cellular uptake and binding to the target molecule. In many cases small molecule delivery may be assessed through functional analyses of effects caused by binding to its receptor. For example, the small molecule may be an agonist or an antagonist and downstream effects can be measured using methods that are well known to those skilled in the art.

The introduced agent may comprise a cellular imaging probe, for example a contrast agent for in vivo imaging such as quantum dots, superparamagnetic iron oxide; or a receptor ligand, for example for an intracellular receptor, for example a nuclear hormone receptor; or a nucleic acid based imaging probe, as noted above, all of which will be well known to those skilled in the art. Methods used to determine the location of imaging probes are well known to those skilled in the art and include, but are not limited to, fluorescence imaging and radioactivity monitoring.

The introduced agent and the entry-promoting agent may be covalently joined. Alternatively, the introduced agent and the entry-promoting agent may be provided as a formulation, for example as a non-covalent complex. The formulation may be prepared by mixing the entry-promoting agent and the introduced agent in appropriate ratios and under appropriate conditions of, for example, pH and salt concentration, for example as set out in the examples. The method may, for example, be performed from up to 100 fold molar excess of introduced agent over entry-promoting agent, through using an equal molar concentration of carrier and cargo molecules, to up to 1000 fold molar excess of entry-promoting agent over introduced agent. For example, an appropriate molar ratio of introduced agent (for example nucleic acid, for example oligonucleotide, for example of 10-30 bases in length and entry-promoting agent may be in the range of 1:0.1 to 1:50 or 1:0.5 to 1:1000, for example 1:1 to 1:10 or 1:5, for example around 1:1.5. An appropriate weight:weight ratio of introduced agent and entry-promoting agent may be in the range of 1:0.1 to 1:50 or 1:0.5 to 1:1000, for example 1:1 to 1:10 or 1:5, for example around 1:1.5. The formation of complexes is discussed further below. The pH at which the entry-promoting agent and the introduced agent are mixed/incubated may be a high pH, for example 10-13.5, as discussed further below.

The method of the first aspect of the invention may be performed in vitro. Examples of situations in which the method of the invention may be useful include large-scale batch transfections and experimental transfections, for example for expressing a valuable protein or to understand the role of a gene or conditions that affect the gene or gene product. Also, the method may be used to characterise a microbiological sample. As noted above, the invention may be useful in, for example, functional studies; generation of stable cell lines; gene silencing; DNA vaccination; and drug delivery.

Thus, a further aspect of the invention provides a method for making a target polypeptide (which term, as noted above, includes both peptides and proteins, including covalently modified polypeptides, for example glycosylated polypeptides, as appropriate), the method comprising the step of preparing the target polypeptide from a cell culture of a host cell, wherein the host cell is a host cell that has been transformed (or whose progenitor has been transformed) by an exogenous nucleic acid molecule (which may be a copy of an endogenous nucleic acid molecule, but which typically is a nucleic acid molecule that differs from nucleic acid molecules previously present within the cell) so that the cell synthesises the target polypeptide, wherein the transfection comprises exposing the host cell to the exogenous nucleic acid molecule in the presence of an entry-promoting agent as defined in relation to the first aspect of the invention.

The method may comprise the step of culturing a host cell under conditions for synthesising the target polypeptide, as will be well known to those skilled in the art. Typically the method may be performed in vitro but it will be appreciated that the method may also be performed in vivo, for example in a plant or (non-human) animal.

The selection of appropriate host cell and other factors such as culture conditions may readily be performed by the skilled person for the intended target polypeptide.

The method of the first aspect of the invention may be performed in vivo or ex vivo. For example the method may be performed on a body surface, for example skin or mucosal membrane. The method may be performed on cells that are subsequently introduced or returned to a subject organism, for example mammal, for example human or livestock/companion/laboratory animal.

A further aspect of the invention provides an entry-promoting agent as defined in relation to the first aspect of the invention and an introduced agent as defined in relation to the first aspect of the invention for use in treating a subject in need of the introduced agent.

Similarly, a further aspect of the invention provides the use of an entry-promoting agent as defined in relation to the first aspect of the invention and an introduced agent as defined in relation to the first aspect of the invention in the manufacture of a medicament for use in treating a subject in need of the introduced agent.

A further aspect of the invention provides a method of treating a subject in need of an introduced agent as defined in relation to the first aspect of the invention, the method comprising the step of treating the subject with an entry-promoting agent as defined in relation to the first aspect of the invention and the introduced agent.

The subject may be, for example, a mammal, for example a human or a livestock/companion/laboratory/wild animal.

The skilled person will readily appreciate that the present invention may be useful in relation to a wide range of disease or conditions, for example diseases or conditions in which treatment with siRNA reagents or therapeutic or antigenic polypeptides may be useful. As examples, the invention may be useful in relation to a mouthwash for treating oral viral infections, for example the common cold, for example with the entry-promoting agent and a nucleic acid against the virus strain in question; for treatment of skeletal related diseases, where the entry-promoting agent is combined with polypeptide or nucleic acid and injected into a joint as an emulsion or suspension to treat arthritis; delivery (for example to the skin) of a DNA vaccine (ie DNA encoding an antigenic polypeptide or vaccine against cancer or other disease e.g. analogous to DNA electroporation vaccines into skin (targeting the DC's) but as a topical agent instead; treatment (for example topical treatment) of a skin disease (for example acne, psoriasis) for example a nucleic acid based therapeutic. However, many other uses of the invention are envisaged, for example corresponding to the range of situations in which RNAi, DNA or polypeptide therapeutics are considered to be useful, particularly with delivery to a body surface, as noted above.

A further aspect of the invention provides a kit of parts or composition comprising an entry-promoting agent and an introduced agent as defined in relation to the first aspect of the invention. The kit of parts may be intended to, or composition may, comprise between a 100 fold molar excess of introduced agent over entry-promoting agent, through an equal molar concentration of carrier and cargo molecules, up to 1000 fold molar excess of entry-promoting agent over introduced agent. For example, an appropriate molar ratio of introduced agent (for example nucleic acid, for example oligonucleotide, for example of 10-30 bases in length and entry-promoting agent may be in the range of 1:0.1 to 1:50 or 1:0.5 to 1:1000, for example 1:1 to 1:10 or 1:5, for example around 1:1.5. An appropriate weight:weight ratio of introduced agent and entry-promoting agent may be in the range of 1:0.1 to 1:50 or 1:0.5 to 1:1000, for example 1:1 to 1:10 or 1:5, for example around 1:1.5. Preferences for the entry-promoting agent and introduced agent are as set out above. For example, the introduced agent may be siRNA molecules. The formation of complexes is discussed further below. The pH at which the entry-promoting agent and the introduced agent are mixed/incubated may be a high pH, for example 10-13.5, as discussed further below.

A further aspect of the invention provides a kit of parts or composition of the invention wherein the kit of parts or composition is pharmaceutically acceptable. Thus, the kit components or composition may comprise (or consist of) pharmaceutically acceptable components, as will be well known to those skilled in the art. Entry-promoting agents of the present invention are considered to be pharmaceutically acceptable. PHMB, for example, is already used in, for example, wound dressings.

A further aspect of the invention provides a composition or kit of parts of the invention for use in treating a patient in need of the introduced agent.

A further aspect of the invention provides a composition or kit of parts of the invention for use in an imaging or diagnostic method. For example, as discussed above, the introduced agent may be an agent useful in imaging or otherwise detecting an intracellular component, for example a nucleic acid or protein. Thus, for example, the introduced agent may be an agent that binds specifically to an intracellular component. For example, the introduced agent may be an antibody or antibody fragment typically retaining specific binding affinity for a particular antigen, as well known to those skilled in the art; or a nucleic acid that hybridises with the required degree of specificity to a particular nucleic acid sequence. As will be appreciated, the imaging or diagnostic method is typically a medical imaging or diagnostic method and may typically be performed on the subject or may be performed on a sample obtained from a subject or may be performed on some other sample. For example, the sample may be a food or water sample or other environmental sample, as will be well known to those skilled in the art.

Thus, for example, an entry-promoting agent of the invention and an introduced agent as defined above, for example a nucleic acid/analogue or nucleobase oligomer, may be used in the detection of an intracellular molecule, for example in the detection of a polypeptide or a nucleic acid sequence, for example by in-situ hybridisation, for example where the delivered nucleic acid is labelled with a fluorophore or other detectable molecule.

The kit of parts or composition of the invention may further comprise a cell for receiving the introduced agent. The cell may be, for example, a cell useful in expressing a polypeptide whose expression is encoded or induced by the introduced agent.

In an embodiment, the entry promoting agent and delivered molecule may be provided together in a buffer having a high pH. Thus, the method for promoting entry of an agent (introduced agent) into a cell may comprise the step of exposing the cell to the introduced agent in the presence of an entry promoting agent (all as set out above) wherein the introduced agent and the entry promoting agent have been mixed or incubated at high pH, for example in a buffer having high pH. The term "high pH" will be well known to the skilled person and typically indicates a pH of above 9, for example above 9.5 or above 10, for example between 10 and 13.5. Typically the introduced agent and the entry promoting agent are mixed at high pH to form nanoparticles, before exposing the cell to the introduced agent in the presence of the entry promoting agent.

Figure 34:
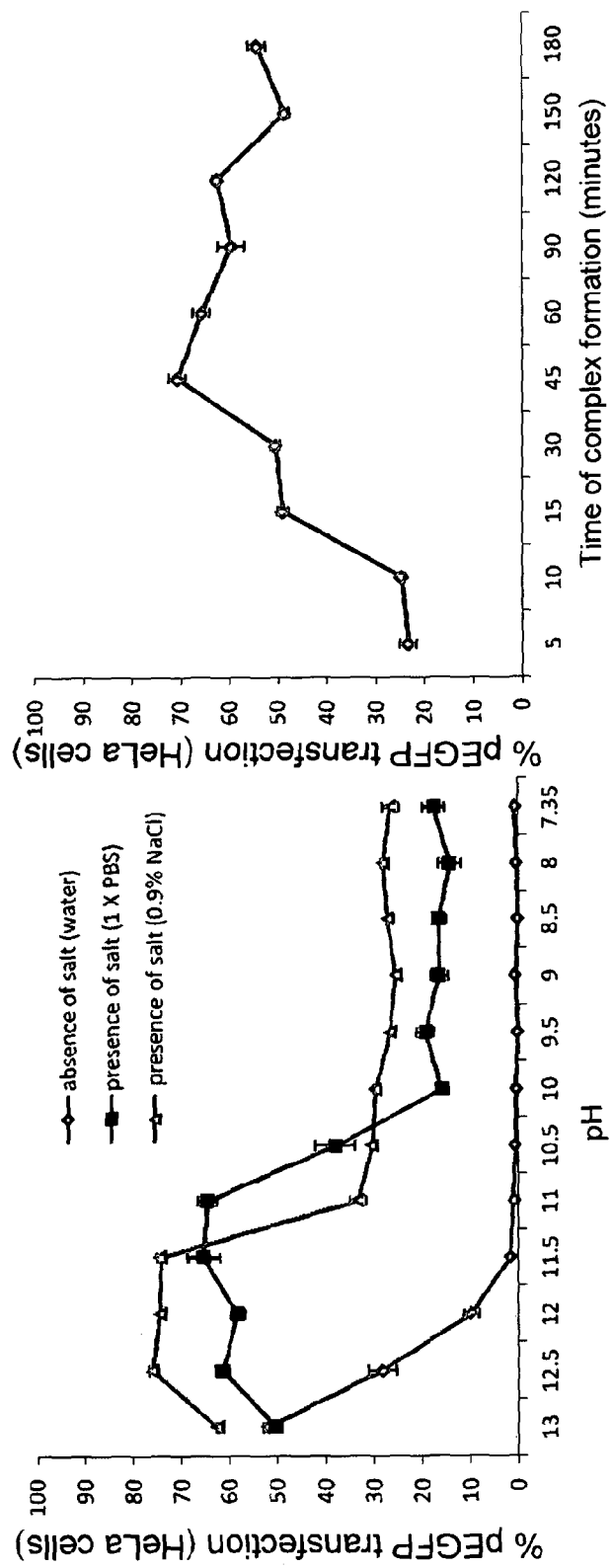

Specifically, buffers (with or without added salts, for example as commonly used in molecular biology buffers, for example PBS; NaCl; or many others) in the range of pH 10-13.5 are considered to provide formulations with improved transfection efficiencies (as shown in FIG. 34). Resulting complex can be diluted 1:1 to 1:1000 in a suitable growth medium, even complex can be added at several time points to cells (repeated multiple transfection) to achieve more efficiency. The procedure involves separate dilution of both the entry promoting agent and the delivered molecule in buffers with high pH and mixing them to form nanoparticles. Ratios and concentrations of the entry promoting agent and the introduced agent may be as discussed above in relation to preparation of a formulation and non-covalent complex; and in relation to the kit of parts.

For example, the following procedure can be used:

Dilute 1-100 μg of the entry promoting agent in buffer, for example 50 μl. Dilute 0.01-50 μg of plasmid DNA in for example 50 μl of buffer. Mix these two solutions and incubate, for example at room temperature for 1 minute to several hours. This mixture can then be used in transfection reactions, using well know methods. Add an appropriate volume of growth medium to the entry promoting agent/delivered molecule mixture, mix and add to cells growing in culture. Transfection will occur as the cell culture is incubated under appropriate conditions know to those working with cell culture.

Those skilled in the art will appreciate that high pH buffers can be easily prepared using, for example, NaOH or KOH. These buffer conditions provide improve transfection efficiencies when using typical complexation times, for example 30 minutes. Therefore, high pH buffers (and the entry promoting agents set out herein) can be easily incorporated into the protocols currently used by researchers.

A further aspect of the invention provides a method for preparing a complex comprising an entry promoting agent (for example PHMB) and an introduced agent as defined above, the method comprising incubating the entry promoting agent and the introduced agent in a complexation buffer, for example at a high pH, for example at a pH of 10-13.5. It is considered that nanoparticles are formed comprising the entry promoting agent (for example PHMB) and the introduced agent, for example oligonucleotide polymers (DNA, PNA, siRNA), proteins, peptides and small molecules. Specifically, formation of nanoparticles can be achieved by incubating PHMB and similar molecules as described above with oligonucleotides, proteins, peptides and small molecules in an appropriate buffer prior to use with cells. An appropriate incubation buffer may include water, PBS, and other buffers used commonly in laboratories. High pH buffers are described above. The optimal buffer may depend on the specific identity of both the entry promoting agent and the delivered molecule, as will be apparent to those skilled in the art. Nanoparticle formation and cell delivery typically is achieved by dilution of both partner molecules in complexation buffer prior to mixing the two components. Also, mixing of the two components typically is carried out prior to combination with other excipients or active ingredients and application to cells or use in vivo. Efficient nanoparticle formation is considered to occur within seconds or minutes but the procedure may be carried out over a number of hours. An appropriate ratio for efficient nanoparticle formation varies with different partner combinations. For example, 1-20:1 (wt:wt) for PHMB:plasmid DNA provides efficient nanoparticle formation. Examples are given above for PHMB; DNA combinations that result in nanoparticle formation. A person skilled in the art will be able to assess nanoparticle formation and delivery efficiencies when using different partner molecule ratios. Nanoparticle formation can be assessed in a number of ways. For example, an individual skilled in the art will be able to assess nanoparticle formation using dynamic light scattering (DLS) and microscopy methods.

A further aspect of the invention provides a complex comprising an entry promoting agent (for example PHMB) and an introduced agent as defined above, wherein the complex is obtainable (or obtained) by a method comprising incubating the entry promoting agent and the introduced agent in a complexation buffer, for example at a high pH, for example at a pH of 10-13.5.

The complexation buffer may in each case alternatively or in addition comprise a cross-linking agent, for example as set out in FIG. 40, for example 1,4-butanediol glycidylether or similar.

The invention is now described in more detail by reference to the following, non-limiting, Figures and Examples.

Figure 2:
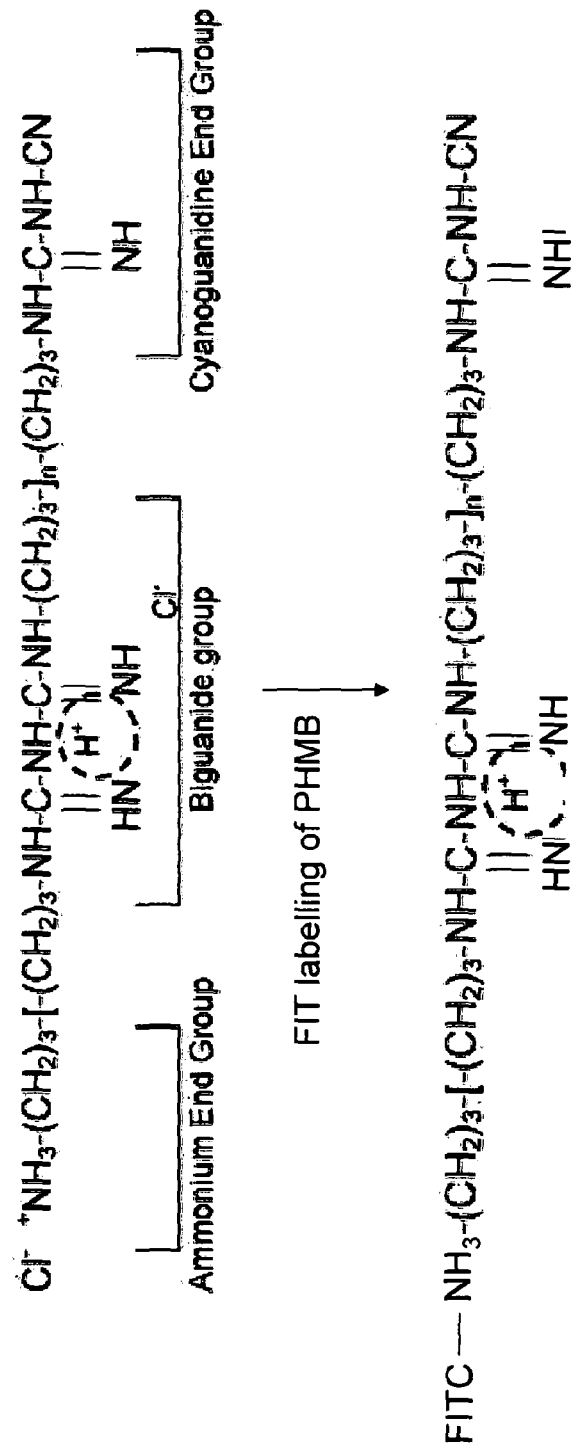
Figure 3:
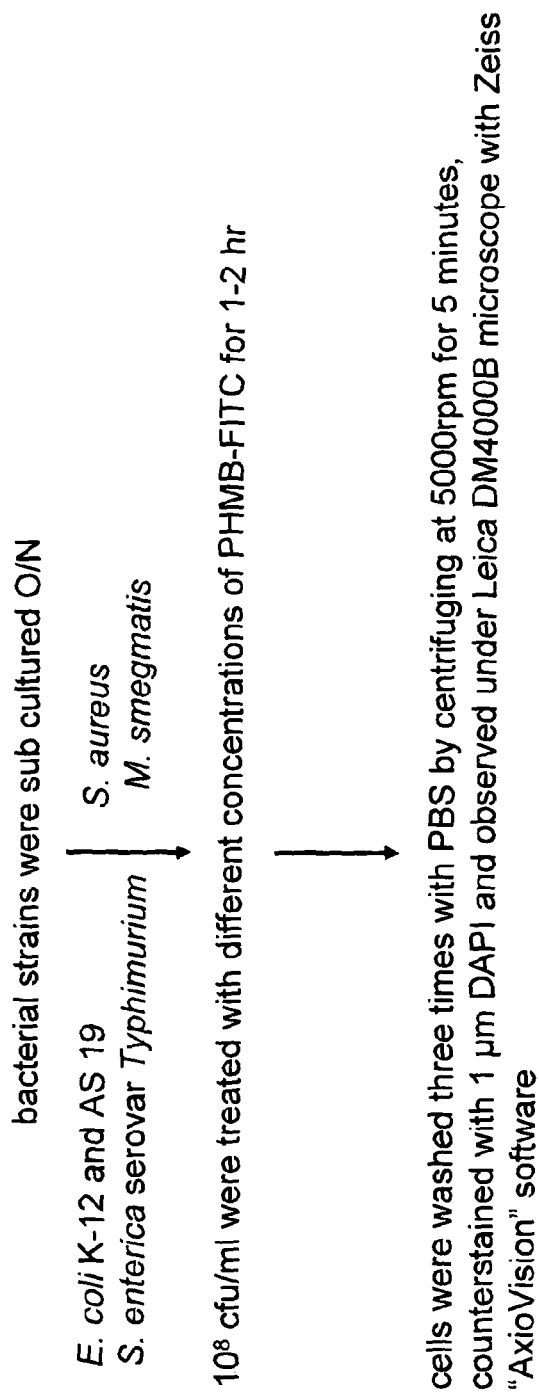
Figure 4:
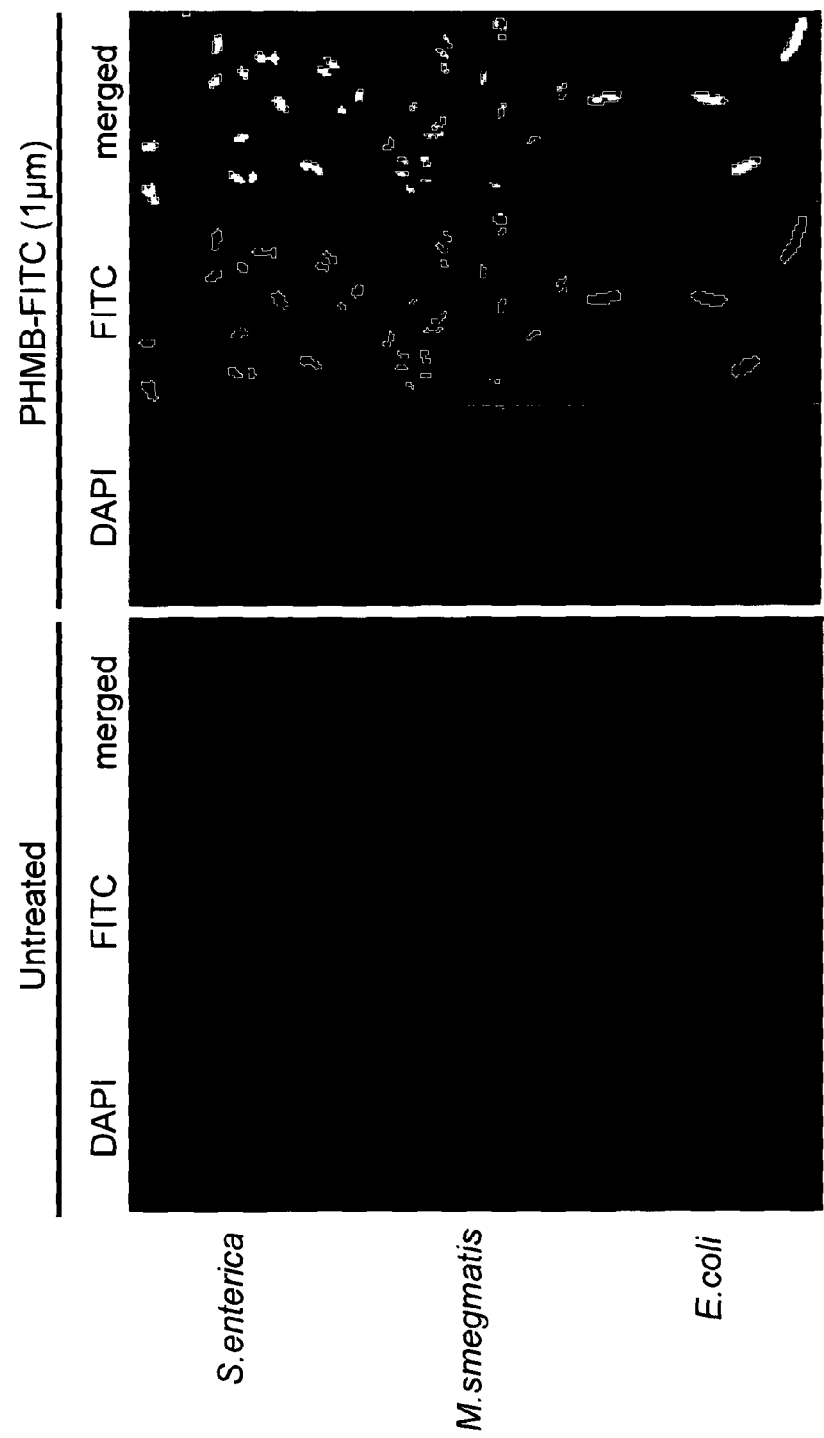

FIGS. 1a and 1b PHMB and possible mechanism of action of PHMB as an antibacterial agent FIG. 2 Conjugation of PHMB with FITC FIG. 3 Uptake of free PHMB into bacterial cells FIG. 4 PHMB enters into wide variety of bacterial cells.

Uptake of PHMB into Gram negative and acid fast bacteria: overnight cultures were treated with 1 µM PHMB-FITC, for 1 hr and counter stained with DAPI before observing under fluorescence microscope. PHMB has entered into all the cells as shown by the presence of green cells under FITC filter.

Figure 5:
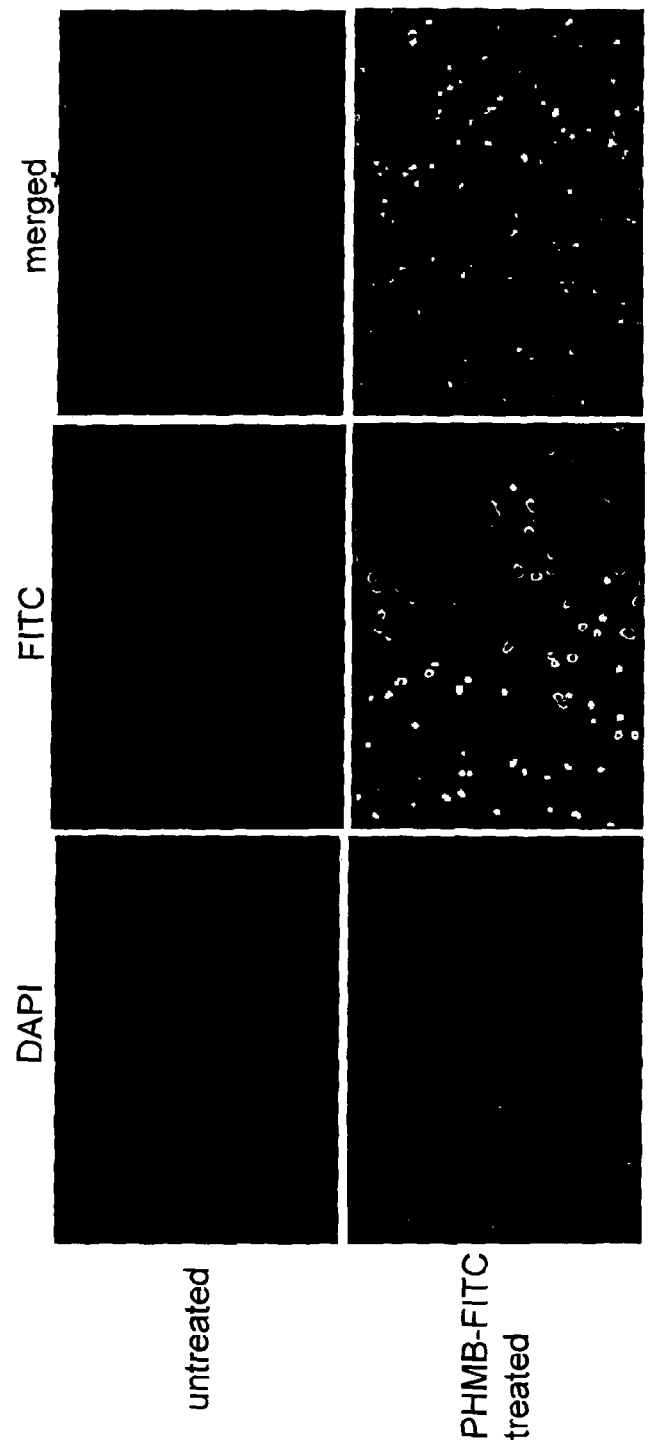

FIG. 5 PHMB-FITC enters into Gram positive bacteria

Uptake of PHMB inot Gram positive bacterial cells: Overnight cultures of *S. aureus* wild type were treated with 1 µM PHMB-FITC, for 1 hr and counter stained with DAPI. All the cells in a given field are positive for PHMB uptake, indicating the efficient cell penetration.

Figure 6:
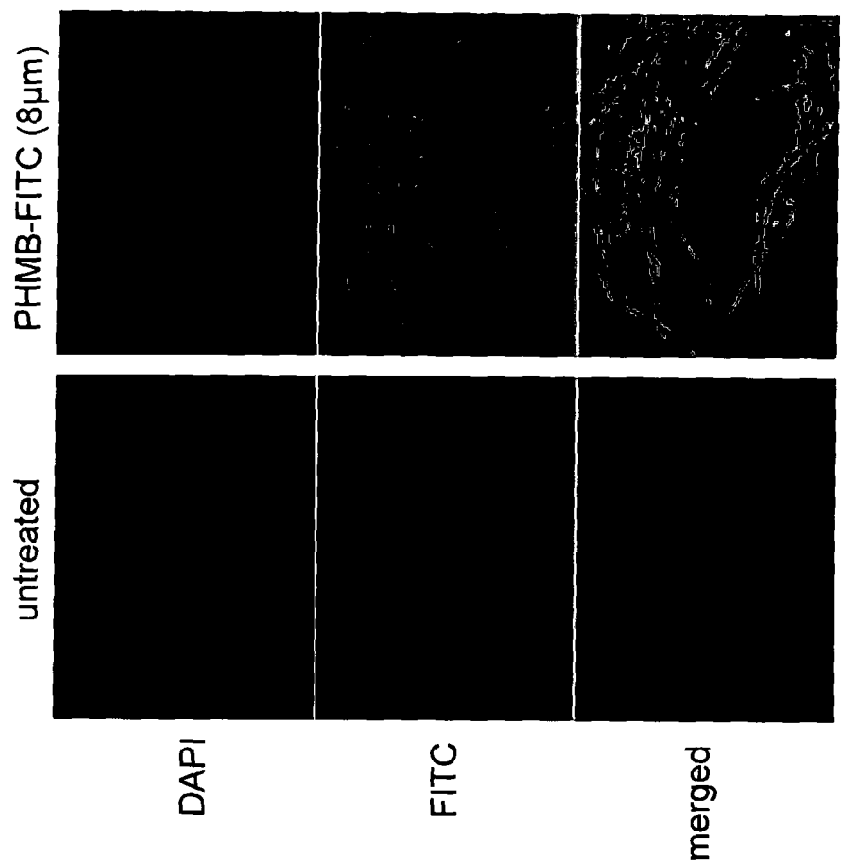

FIG. 6 PHMB enters efficiently into fungi

*Aspergillus fumigatus* vegetative cells were treated with PHMB-FITC. It is apparent that the PHMB enters into all the cells.

Figure 7:
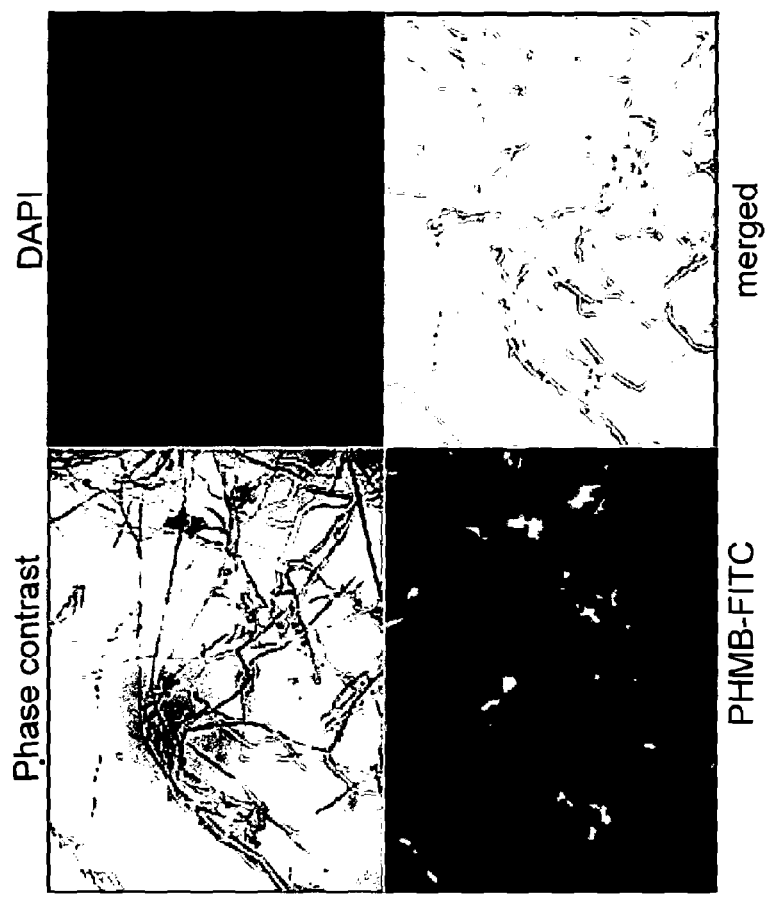

FIG. 7 Phase contrast image of PHMB treated *Aspergillus fumigatus*

Phase contrast images showing the fungal hyphae and entry of PHMB into most of the hyphae.

Fungal cells are relatively difficult to transfect. Uptake of PHMB into *Aspergillus* hyphae show the potential utility of this molecule as a carrier for fungi.

Figure 8:
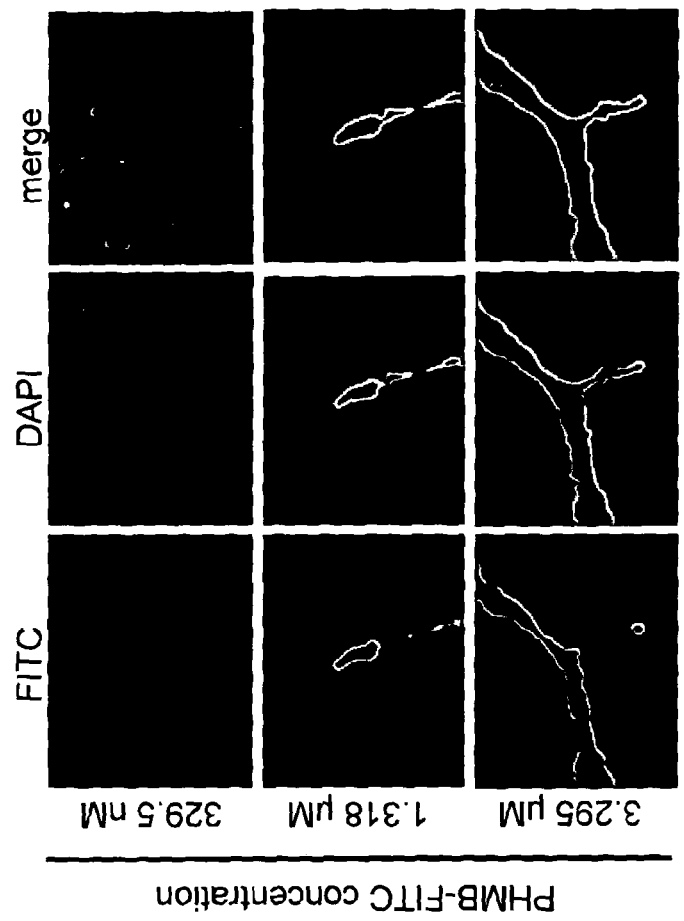

FIG. 8 Entry of PHMB into *Aspergillus fumigatus*

FIG. 9 Uptake of free PHMB into mammalian cells

Figure 10:
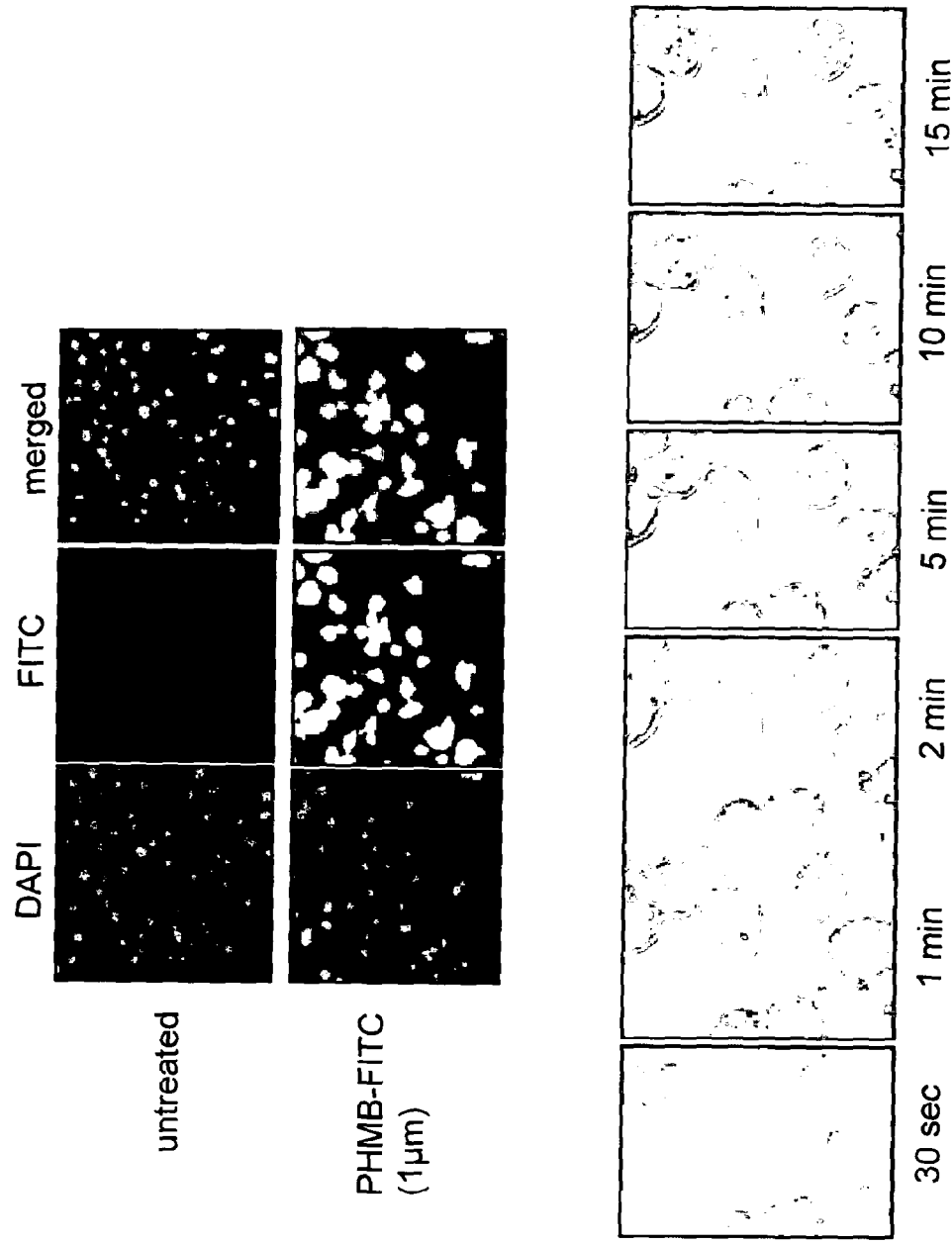

FIG. 10 PHMB enters into mammalian cells at a rapid rate

Uptake of free PHMB-FITC into J774 macrophages. Upper panel: fluorescence microscopy images of PHMB-FITC uptake. Lower panel: confocal images of time course measurements of PHMB uptake. PHMB starts entering the cells in less than 10 minutes.

Figure 11:
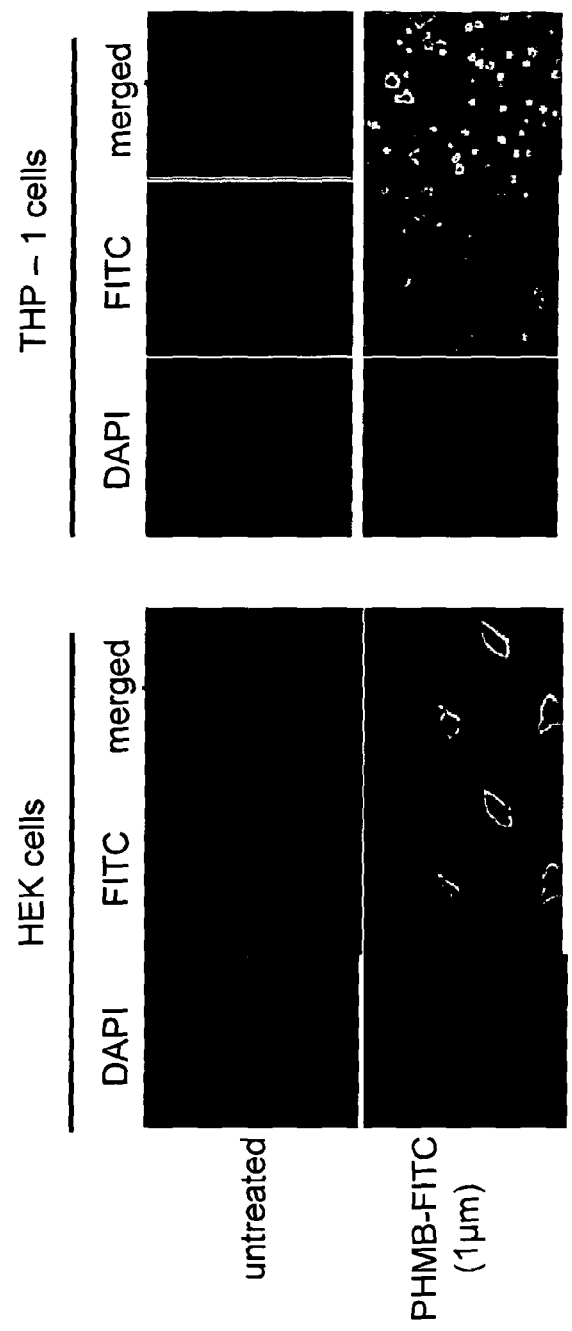

FIG. 11 PHMB enters efficiently into adherent as well as suspension cells

Left panel: uptake of PHMB into adherent cells (HEK 293). Right panel: uptake of PHMB into suspension cells (THP-1 monocytes).

Figure 12:
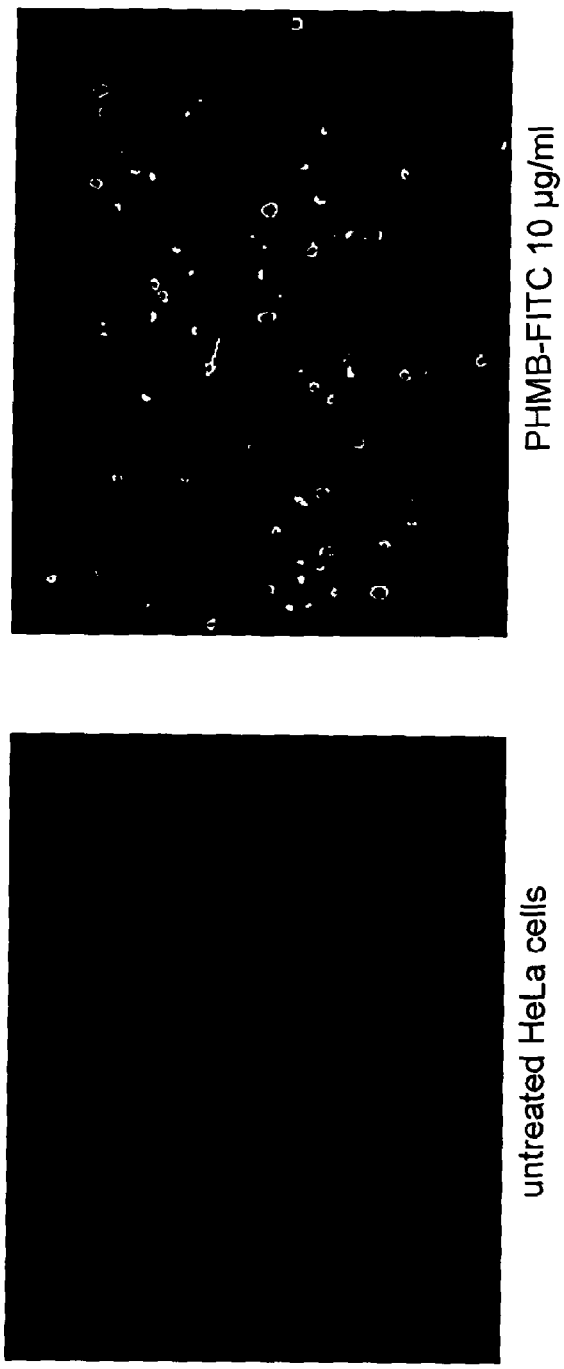

FIG. 12 PHMB localizes to cytoplasmic compartment.

Cytoplasmic localization of PHMB in mammalian cells: HeLA cells treated with 10 µg/ml PHMB-FITC for 2 hr were observed under inverted fluorescence microscope, the arrow pointing the cytoplasmic localisation of the fluorescence. There is only background fluorescence in untreated cells compared to PHMB treated cells, where all the cells are positive for uptake.

Figure 13A:
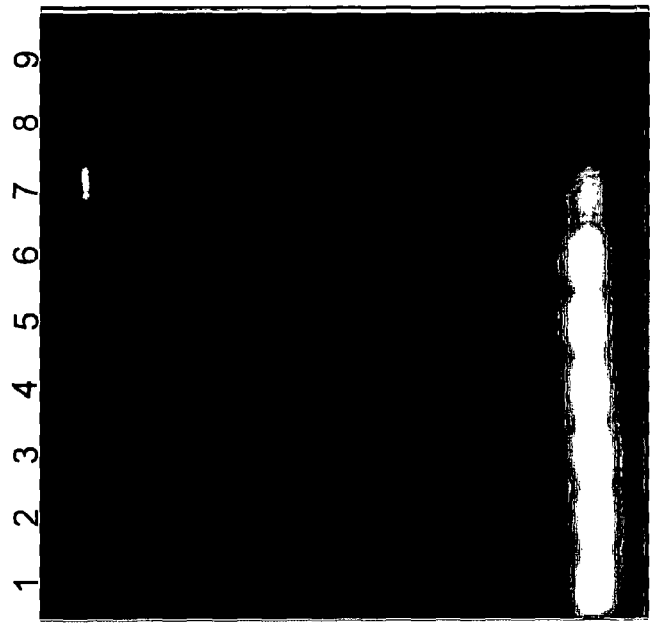
Figure 13B:
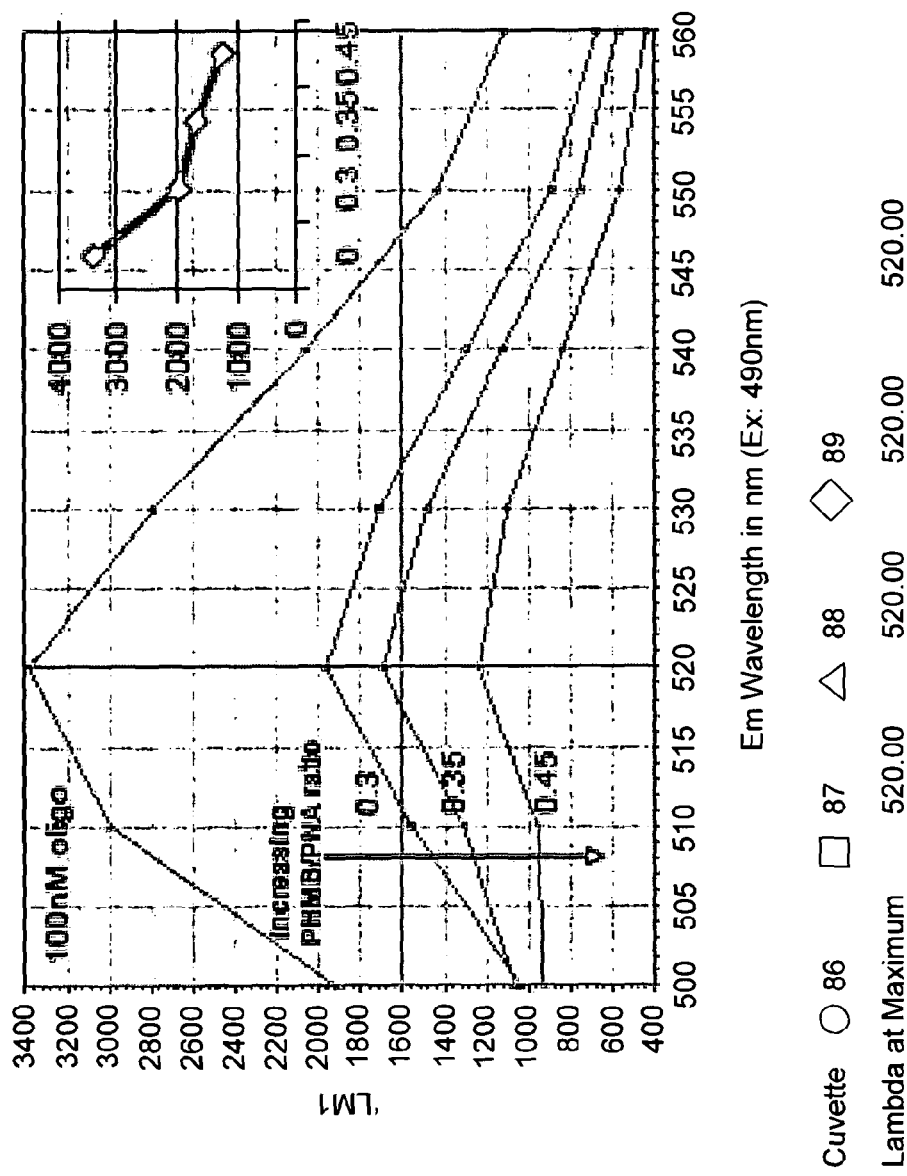

FIGS. 13a and 13b Interaction of PHMB with oligonucleotides

Evidence for the interaction of PHMB with nucleic acids: left panel shows the electrophoretic mobility of FAM labelled oligonucleotide. Lane 1: Oligo oly, Lane 2-8: increasing PHMB/oligo molar ratio: L2: 0.02, L3: 0.06, L4: 0.12, L5: 0.2, L6: 0.4, L7: 0.8, L8: 1.6. Addition of PHMB results in the retardation of oligonucletoide migration, as evident in lane 5-7. At PHMB/oligo molar ratio 0.8, there is a complete retardation in the migration, indicating an efficient nucleic acid binding. Right panel shows the spectroscopic evidence for the interaction of PHMB with FAM labelled oligonucleotide. Addition of PHMB results in quenching of FAM fluorescence, which occurs when both molecules are in close proximity, showing the interaction.

Figure 14:
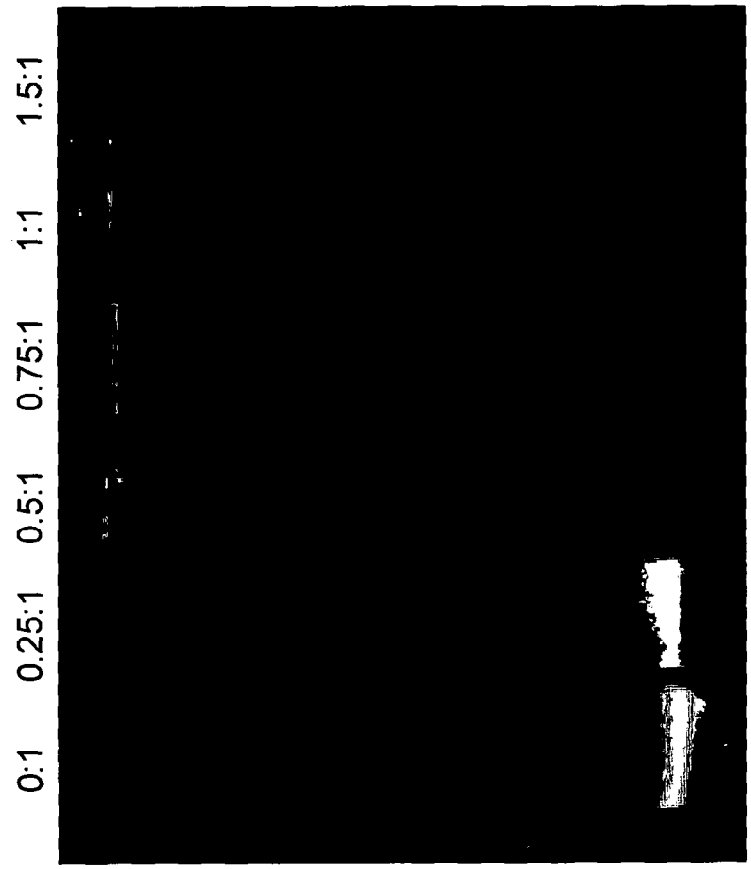

FIG. 14 Interaction of PHMB with plasmid DNA

Evidence for the interaction of PHMB with plasmid DNA: The complex of PHMB/plasmid (encoding GFP)

were prepared at different w/w ratio and incubated for 30 min at 37° C., then run on 1% agarose gel stained with ethidium bromide (0.5 µg/ml). It is observed that addition of PHMB results in retardation of migration of plasmid DNA 9 Lane 3-5). Complete retardation is observed at 2/2 ratio 1.5:1. This ratio was used as a guide for transfection experiments.

Figure 15:
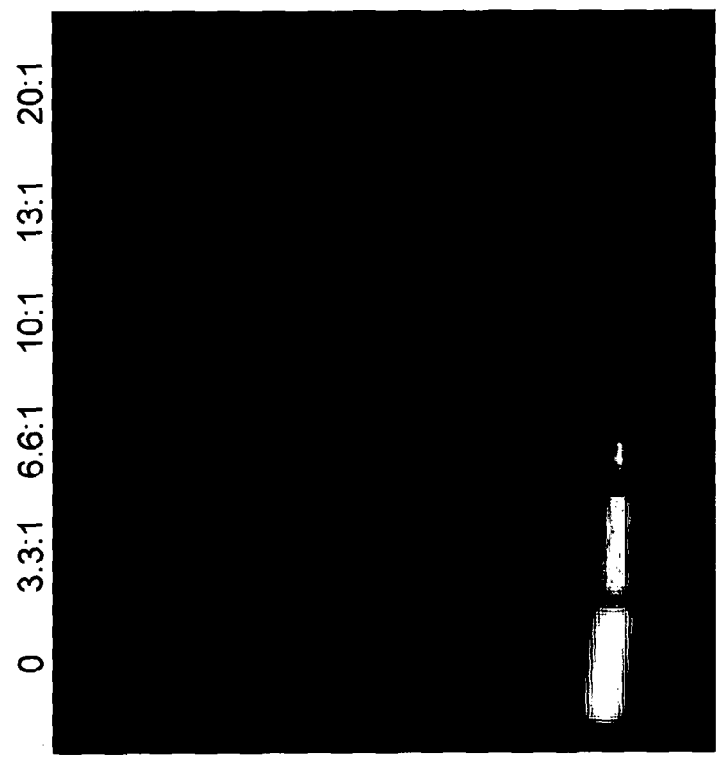

FIG. 15 Interaction of PHMB with siRNA

Evidence for the interaction of PHMB with siRNA: PHMB/siRNA complex were prepared at different molar (M/M) ratio. It is observed that the addition of PHMB resulted in retardation of migration of siRNA. At molar ratio 20:1 complete retardation in migration is observed. This ratio was used as a guideline for siRNA delivery.

Figure 16:
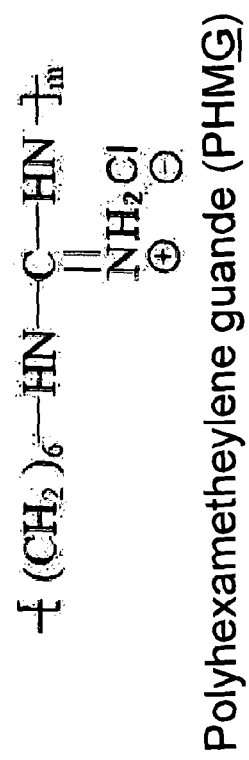

FIG. 16 Interaction of PHMB analogues with nucleic acids

Figure 17:
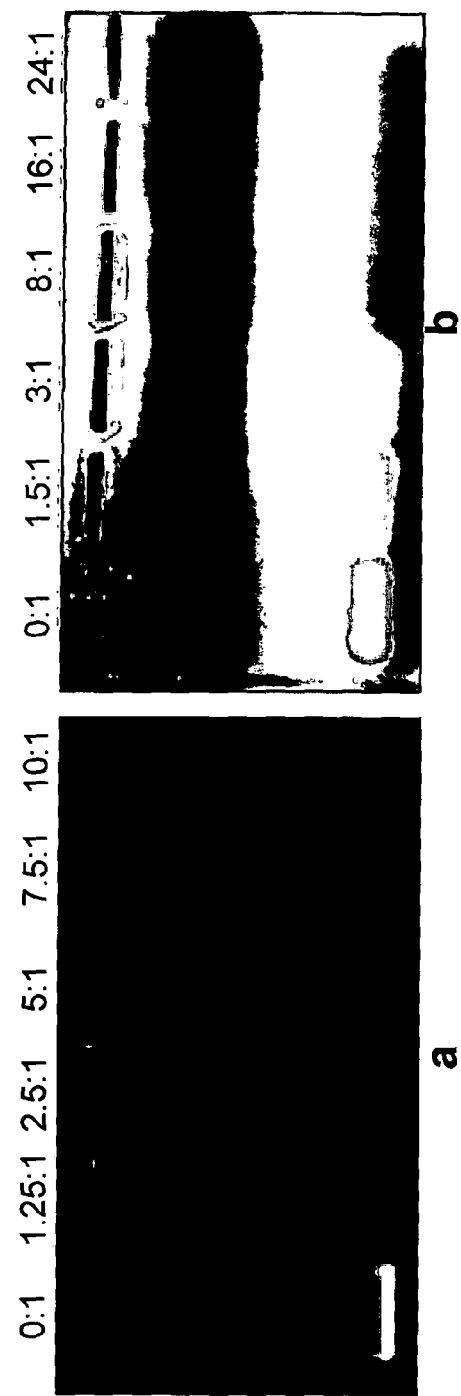

FIG. 17 Interaction of polyhexamethylene guanidine (PHMG) with nucleic acids

Gel shift assay to show the interaction of PHMG with nucleic acids. PHMG/plasmid (a) and PHMG/siRNA (b) complex were run on the agaraose gel. Complete retardation was observed for whole plasmid (w/w 2.5:1) and siRNA (8:1, M/M).

Figure 18:
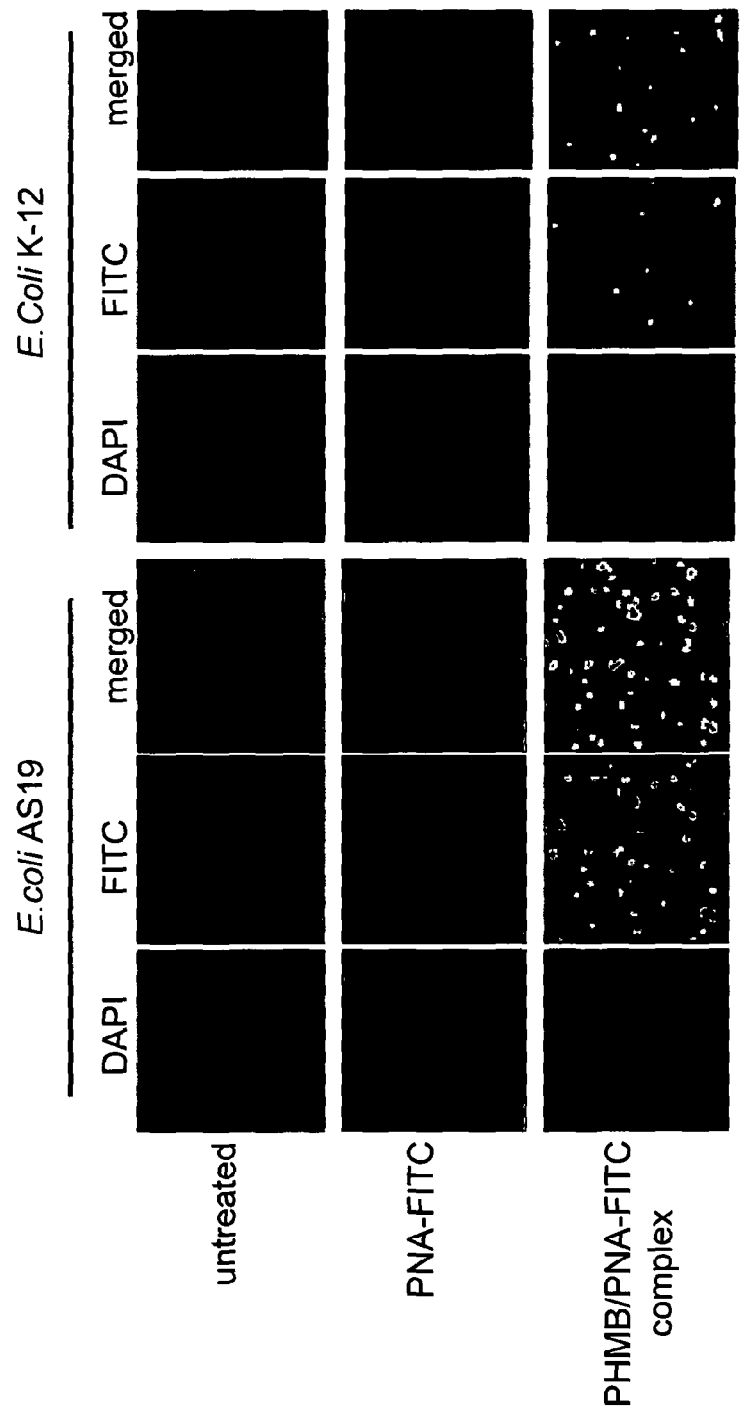

FIG. 18 PHMB carries PNA into bacterial cells through noncovalent complex

Entry of PHMB/PNA-FITC complex into bacteria. E. coli AS19 and K12 strains were treated with PHMB/PNA-FITC complex (molar ratio 11:1), counterstained with DAPI and observed under fluorescence microscope. There is a minimal uptake in PNA alone treated bacteria, as expected. An improvement in the fluorescence intensity and number of positive cells was apparent in cells treated with the PHMB/PNA complex.

Figure 19:
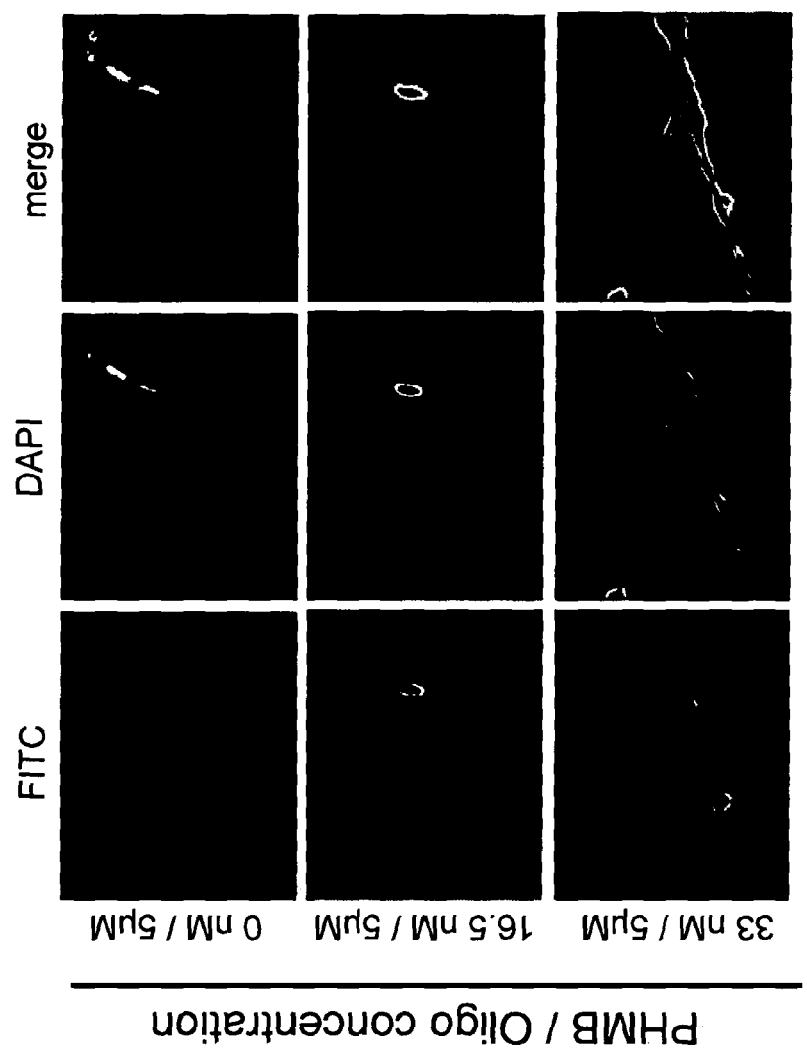

FIG. 19 PHMB carries oligonucleotides into *Aspergillus fumigatus*

Uptake of PHMB/oligonucleotides into fungi. *Aspergillus fumigates* was treated with PHMB/FAM labelled oligo complex, counterstained with DAPI. There is a minimal uptake in oliqonucleotide alone treated samples. Improvement in the uptake is noticed in PHMB/oligo complex treated samples, indicating the delivery of oligonucleotides into fungi.

Figure 20:
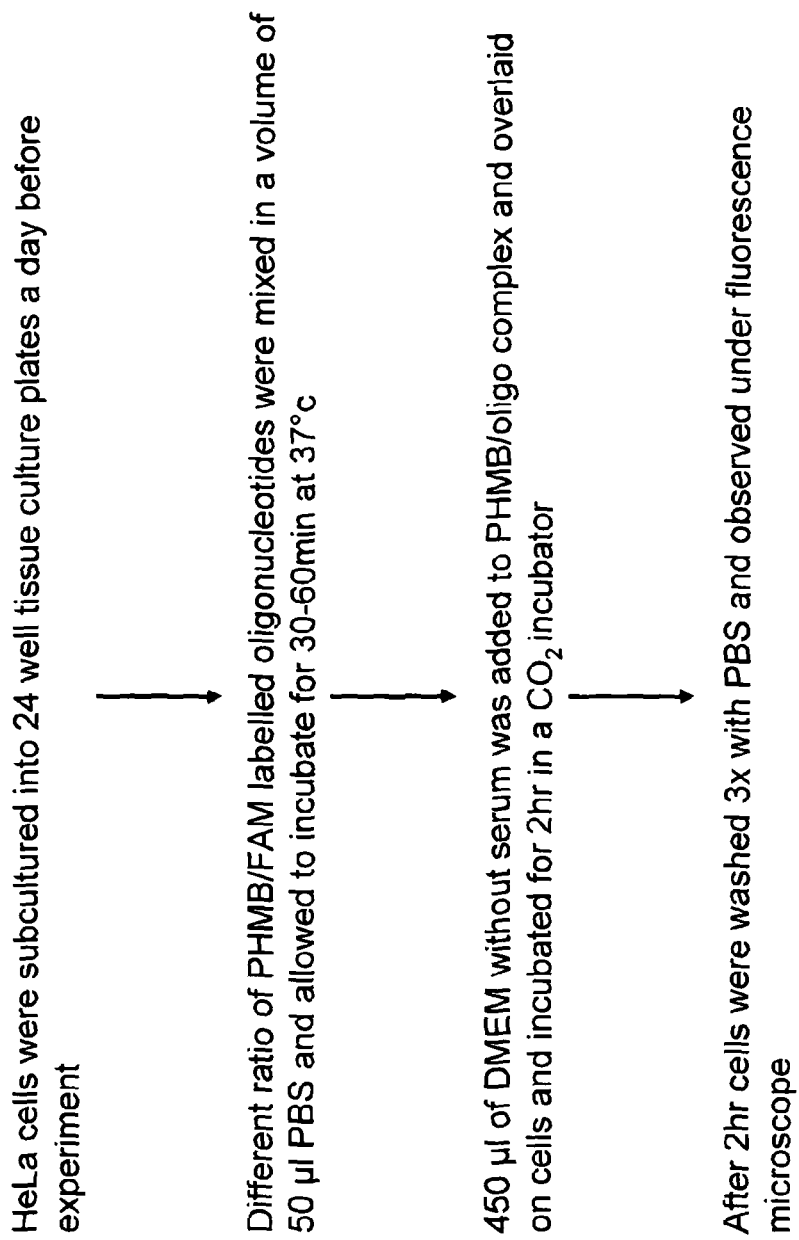

FIG. 20 Delivery of oligonucleotides into mammalian cells

Figure 21:
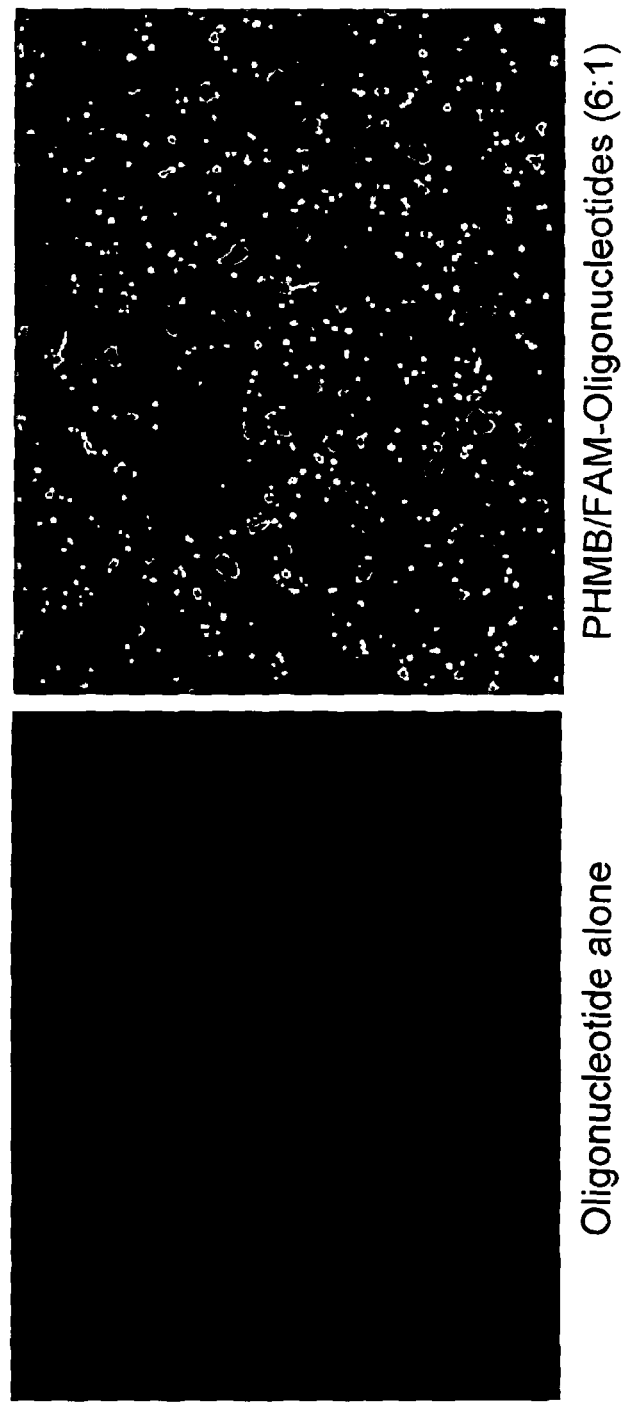

FIG. 21 PHMB carries oligonucleotides into nucleus of mammalian cells

Delivery of oligonucleotides into mammalian cells: HeLa cells were treated with PHMB/oligo complex for 2 hours. There was no uptake in cells treated with fee oligonucleotides, were as the cells treated with PHMB/oligonucleotide showed enhanced uptake. The oligonucleotides were delivered into nucleus as indicated by the arrow.

Figure 22:
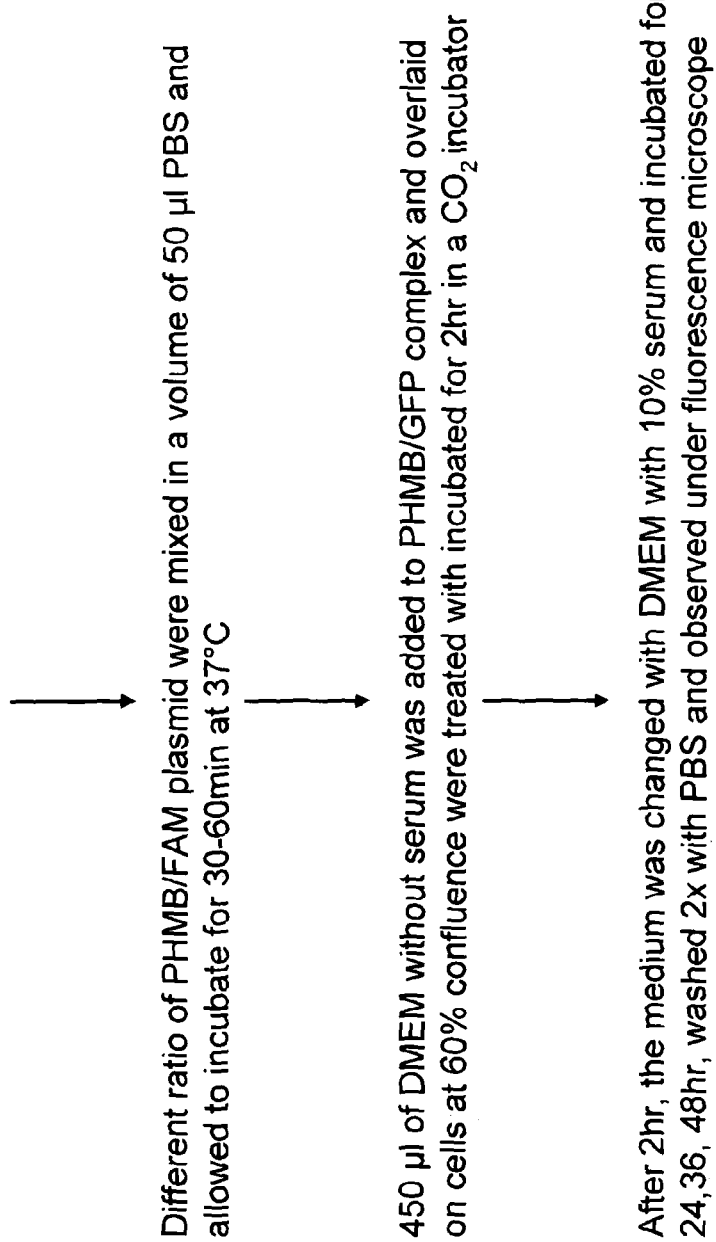

FIG. 22 Delivery of plasmid encoding GFP into mammalian cells

Figure 23:
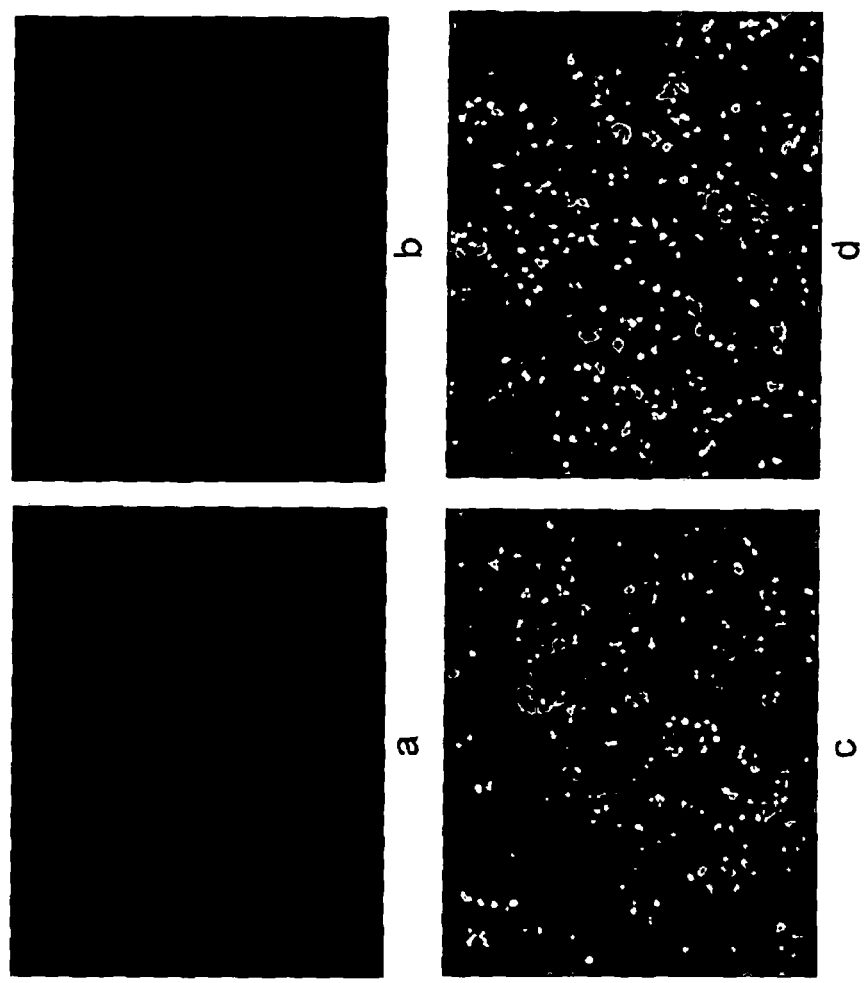

FIG. 23 PHMB-delivered plasmid is able to express GFP in HeLa cells

Delivery of plasmid into mammalian cells. HeLa cells were treated with PHMB/plasmid encoding GFP. There was no expression of GFP in cells untreated (a) or treated with DNA alone (b, 500 ng plasmid). There was an enhanced expression of GFP in PHMB/plasmid treated cells (c, 2.5 µg PHMB+500 ng plasmid). Lipofectamine 2000 was used as positive control (d).

Figure 24:
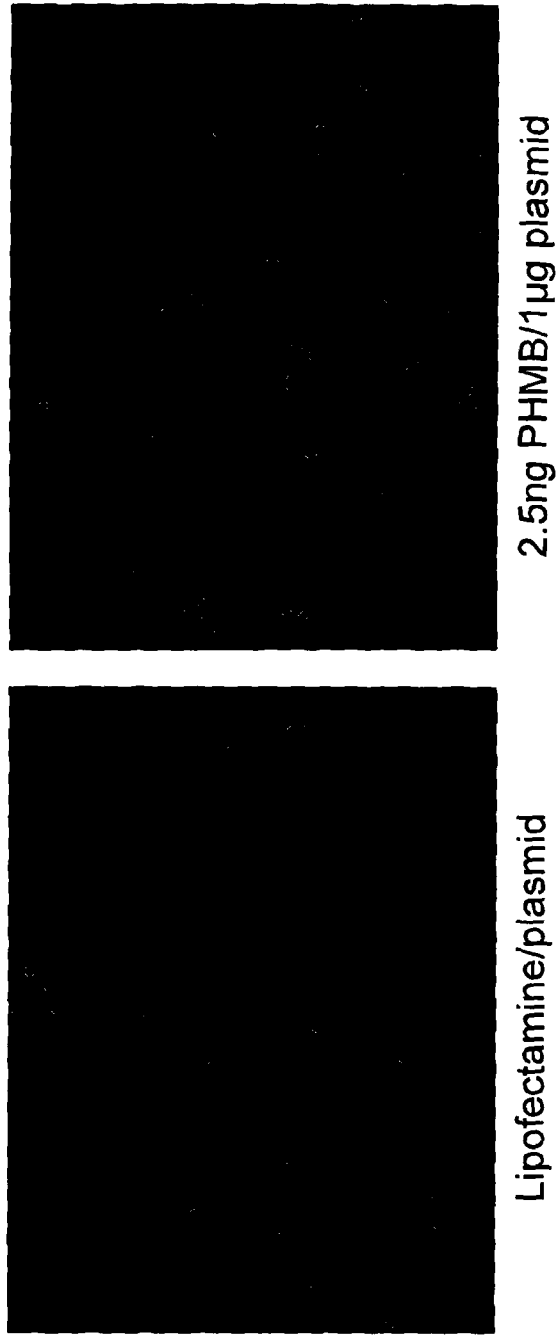

FIG. 24 PHMB-delivered plasmid is able to express GFP in HeLa cells

Figure 25:
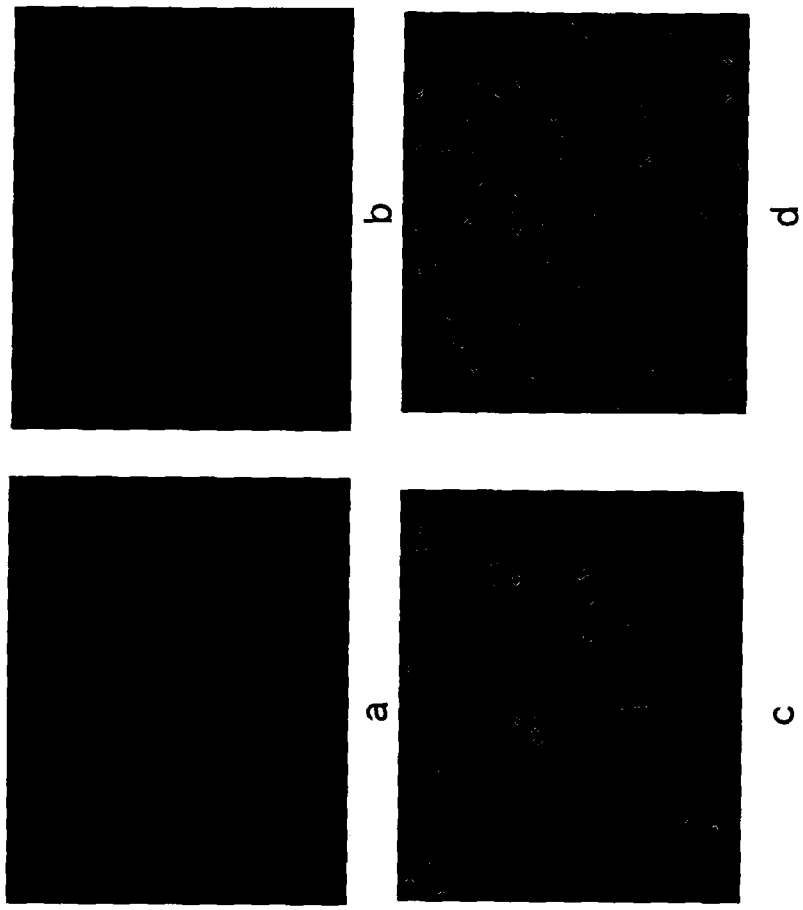

FIG. 25 PHMB delivered plasmid is able to express GFP in osteosarcoma cells

Delivery of plasmid into mammalian cells. Osteosarcoma cells treated with PHMB/plasmid (c, 2.5:1, w/w) express GFP. There is no expression in cells treated with plasmid alone (b) or untreated (a). Lipofectamine 2000 was used as positive control (d).

Figure 26:
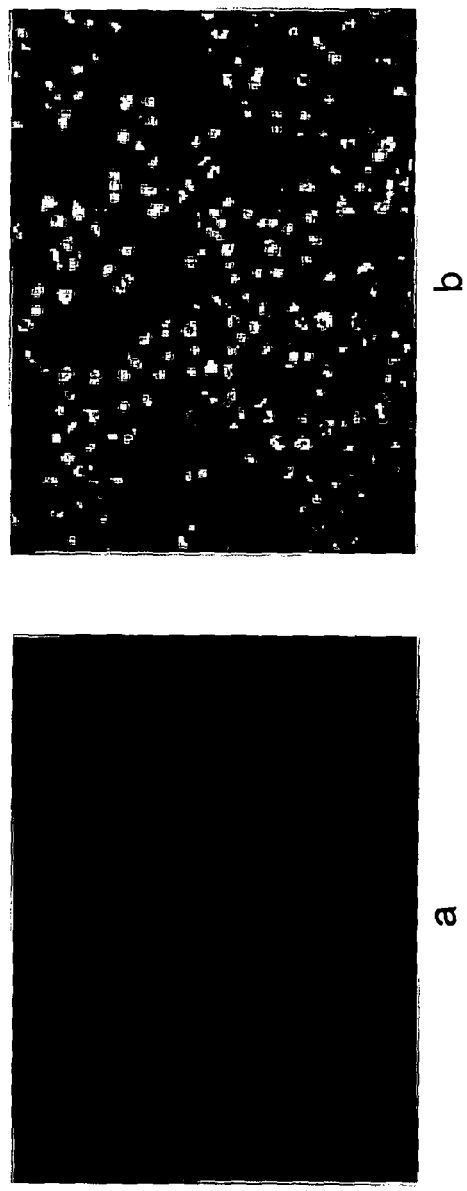

FIG. 26 Uptake of PHMG-FITC into mammalian cells

Cell penetrating property of PHMG: HeLa cells were treated with 3 µg/ml PHMG-FITC(b). PHMG has entered efficiently into all the cells, whereas untreated cells show a minimal background fluorescence (a). It is evident that analogues of PHMB also possess cell penetrating property.

Figure 27:

FIG. 27 PHMG is also able to carry plasmid into mammalian cells

Delivery of plasmid into mammalian cells. Osteoscarma cells treated with PHMG/plasmid (a, 1.25:1) express GFP. This shows the carrier potential of PHMG for mammalian cells. Lipofectamine 2000 is used as a positive control (b).

Figure 28:
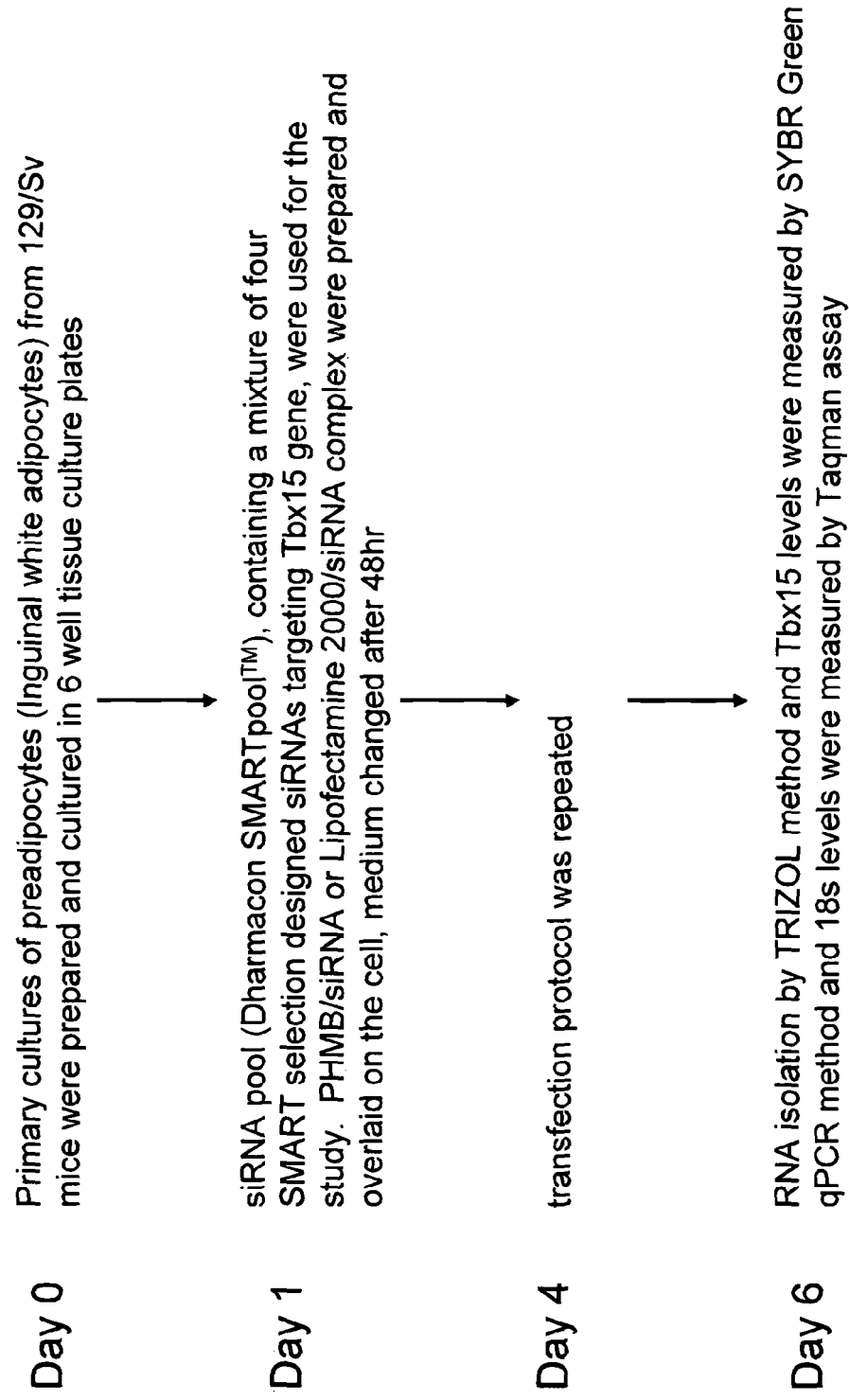

FIG. 28 Delivery of siRNA into primary cells and analysing effects

Figure 29:
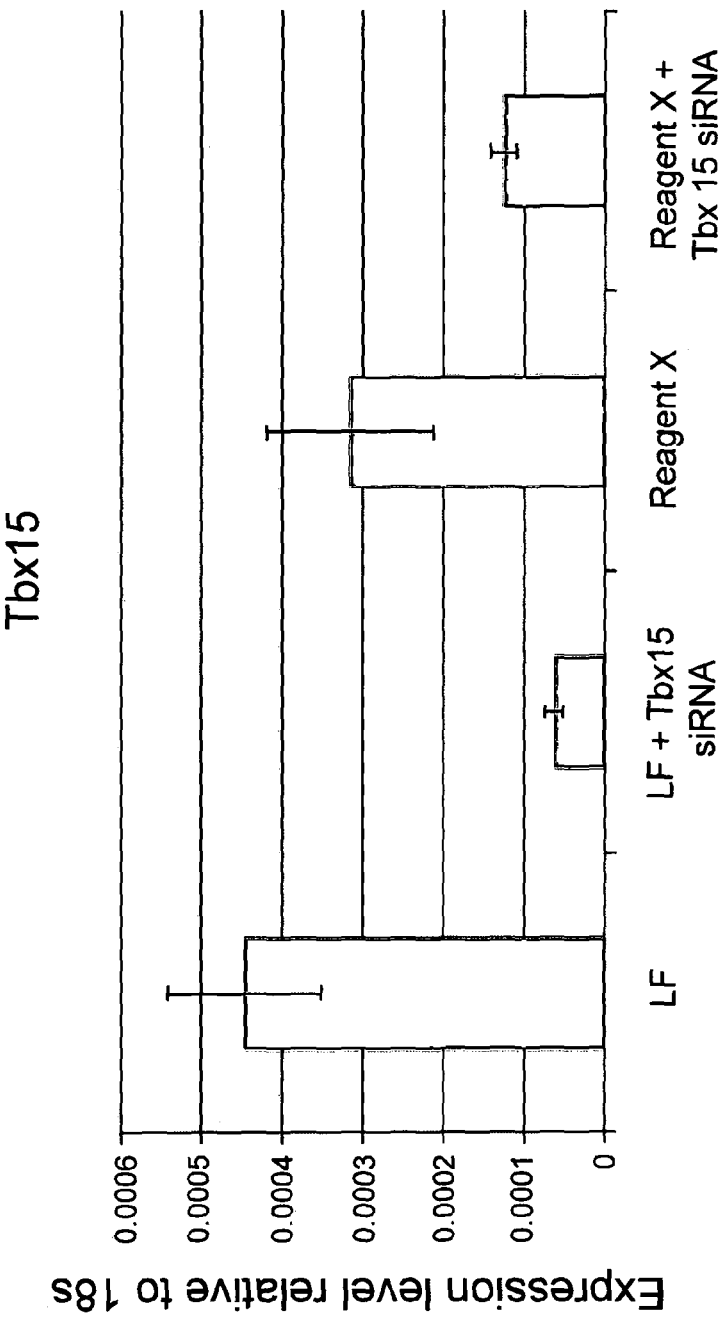

FIG. 29 siRNA delivered by PHMB is able to silence genes in primary cells

Knockdown of Tbx gene in primary adipocytes. Tbx 15 siRNA pool was used to knockdown Tbx 15 mRNA using lipofectamine and PHMB. 60% reduction in Tbx 15 mRNA is observed when PHMB is used.

Figure 30:
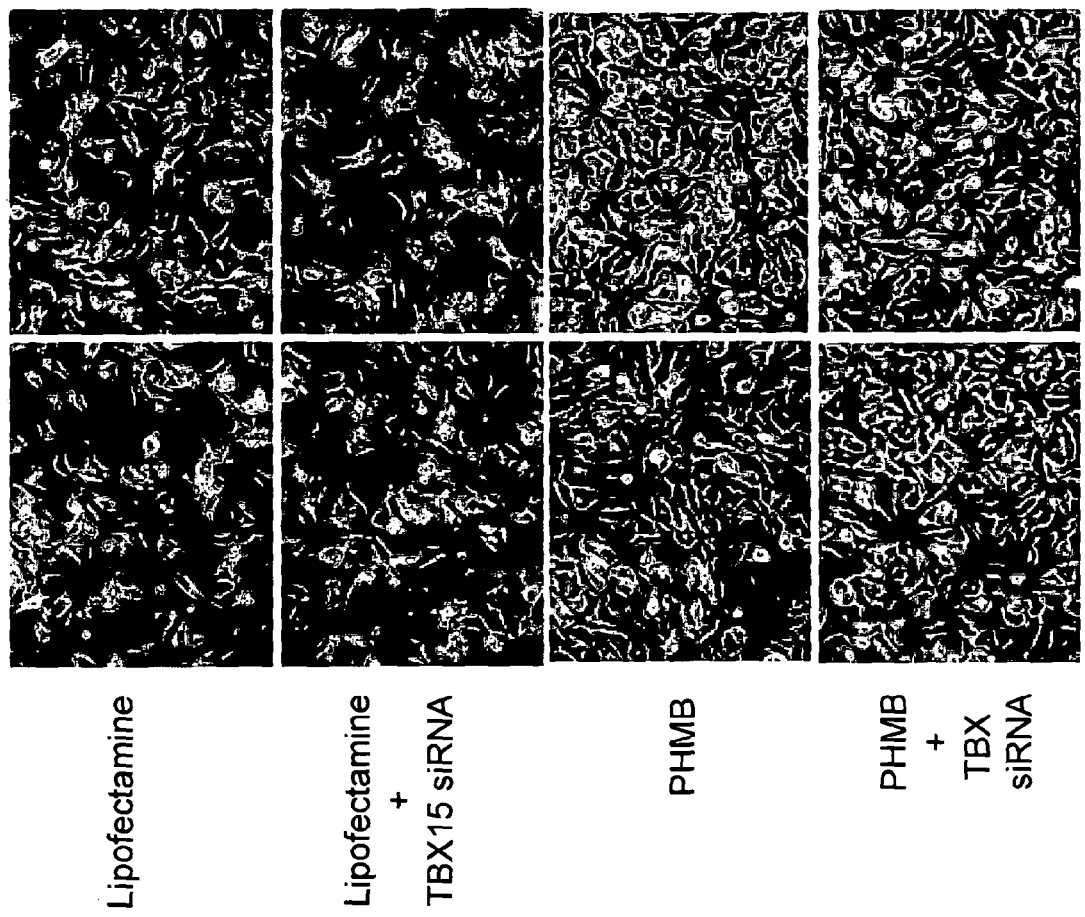

FIG. 30 PHMB is less toxic to primary cells than lipofectamine 2000

Cytotoxicity of carriers in primary cells. Cells were treated with lipofectamine 2000 and PHMB and observed 6 days post treatment. Both lipofectamine and lipofectamine+siRNA treated cells show higher cytotoxic effects than PHMB or PHMB/siRNA treated cells.

Figure 31:
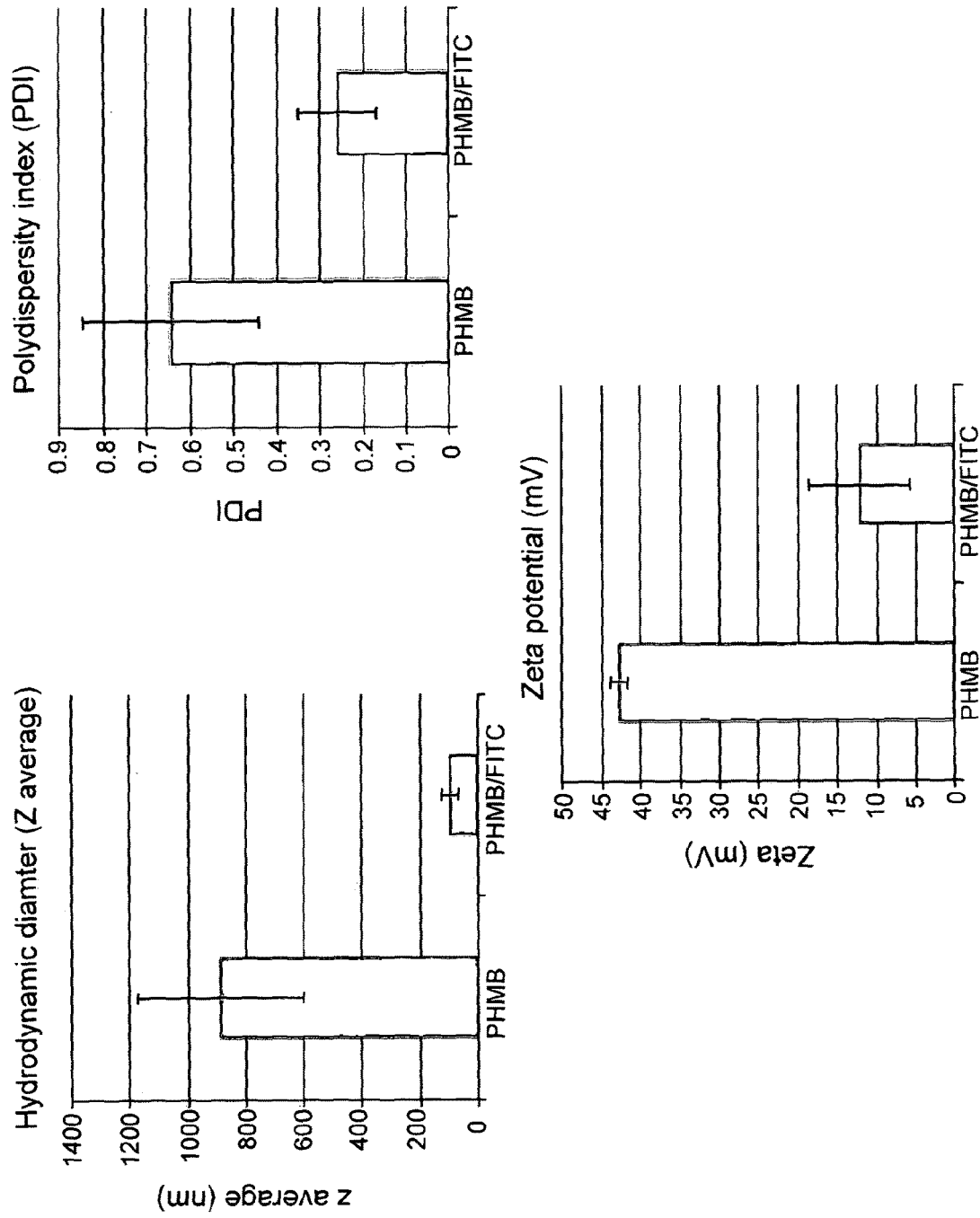

FIG. 31 PHMB forms nanoparticle with FITC

Characterization of particles formed by PHMB and cargo. Noncovalent interaction between a carrier and cargo results in particle formation. PHMB/free FITC complex was prepared in water and the resulting size and surface charge is analysed by dynamic light scattering. It is observed that PHMB alone forms amorphous aggregate of mean size 888.6 nm, with PDI of (0.64) with surface change of +42.8 mV indicating heterogeneous population. PHMB/FITC complex had a mean size of 98.36 nm with PDI of 0.20 indicating formation of homogenous population of nanoparticles, with positive surface charge (+12.2 mV).

Figure 32:
Figure 32:
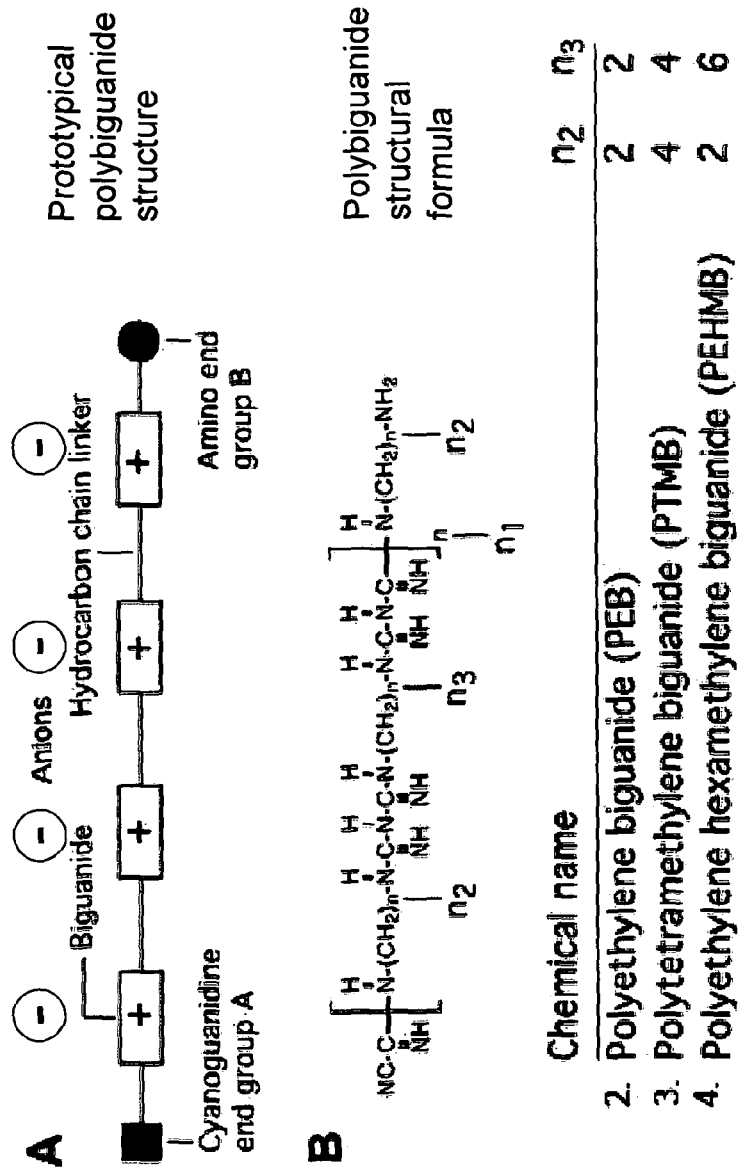

FIG. 32 Analogues of PHMB as a potential transfection reagents

Figure 33A:
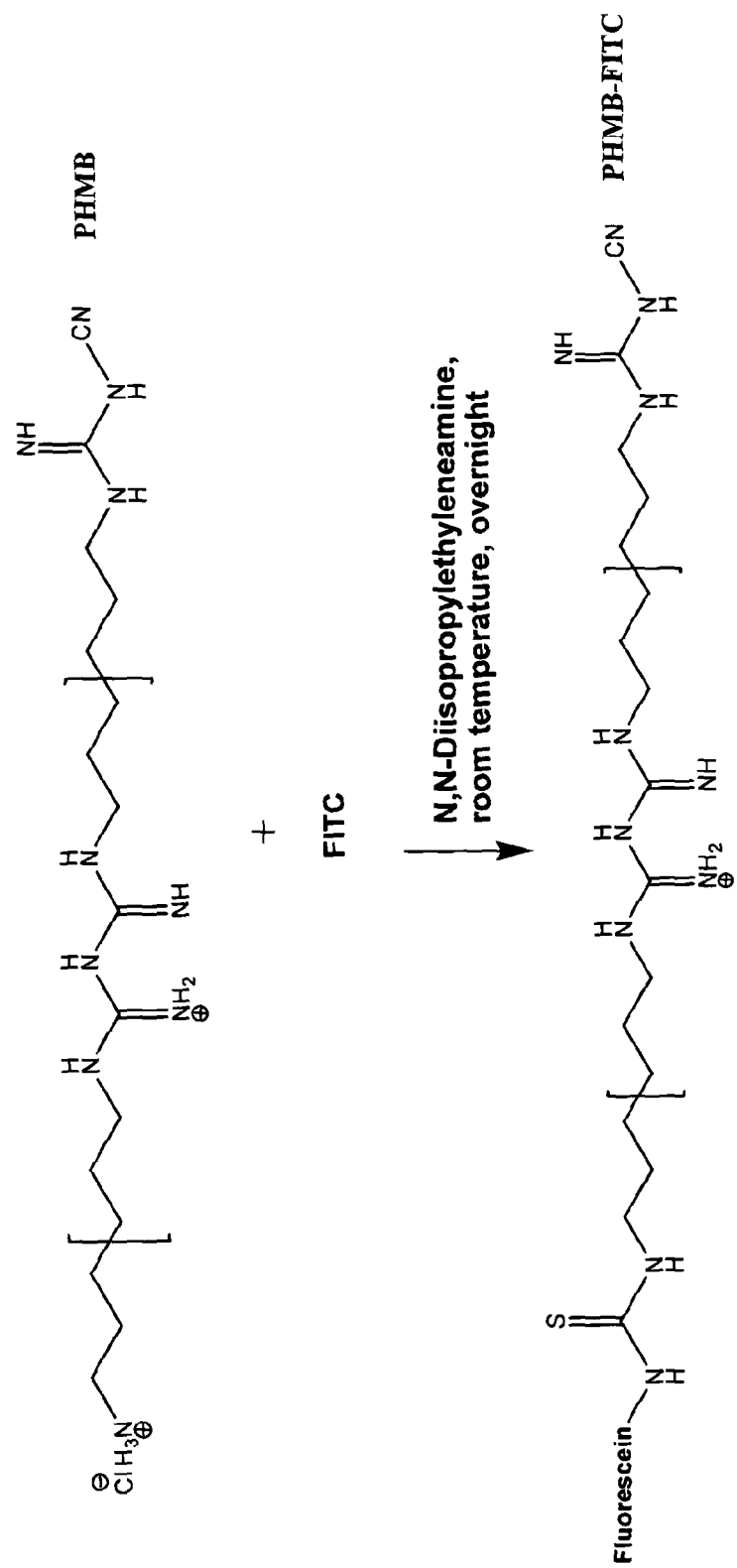

FIGS. 33a and 33b Conjugation of PHMB with FITC, demonstrated by IR spectra

To a solution of 50 mg of PHMB and 50 µl N,N-diisopropylethylamine in 800 µl deionized water, 2 mg of FITC in 100 µl DMF was added. Reaction mixture was shaken at room temperature overnight and then lyophilized, resulting in a residual mass, which was triturated with ethyl acetate to remove excess of unreacted FITC. The resulting material was dissolved in 1 ml of deionized water and dialyzed (cut off 3.5 kDa) against 50% ethanol solution for 5 days with intermittent change of solution (10 times, 500 ml). The dialyzed solution was lyophilized to obtain fluoresceinyl-PHMB. PHMB-FITC conjugation was confirmed by recording IR spectra, IR (Nujol), v (cm−1): 750-760 cm−1 (C=S stretching).

FIG. 34 High pH and salt enhances transfection using PHMB/pEGFP complexes

At left, effect of pH and buffer on complex formation and transfection efficiency was tested by preparing buffers (water or PBS or 0.9% NaCl) with pH from 13.5-7 by using NaOH or HCl. Complex of 4 µg PHMB and 1 µg pEGFP was prepared in 100 µl volume of buffers by incubating at room temperature for 20 minutes and diluted in growth medium, added to 1.5×105 HeLa cells at the time of plating in a 12 well plate. Transfection efficiency was monitored by Flow-cytometry by measuring GFP expression 36 hours post transfection.

At right, to indirectly assess the rate of complex formation between PHMB and pEGFP, multiple complex reactions were prepared by mixing 4 µg PHMB and 1 µg pEGFP in 1×PBS with pH 11.5, and added at different time points to HeLa cells in 12 well plate as describe above. GFP expression was measured by Flowcytometry 36 hours post transfection. PHMB forms complexes with plasmid in less than 5 minutes and the reaction is stable for several hours at room temperature.

Figure 35:
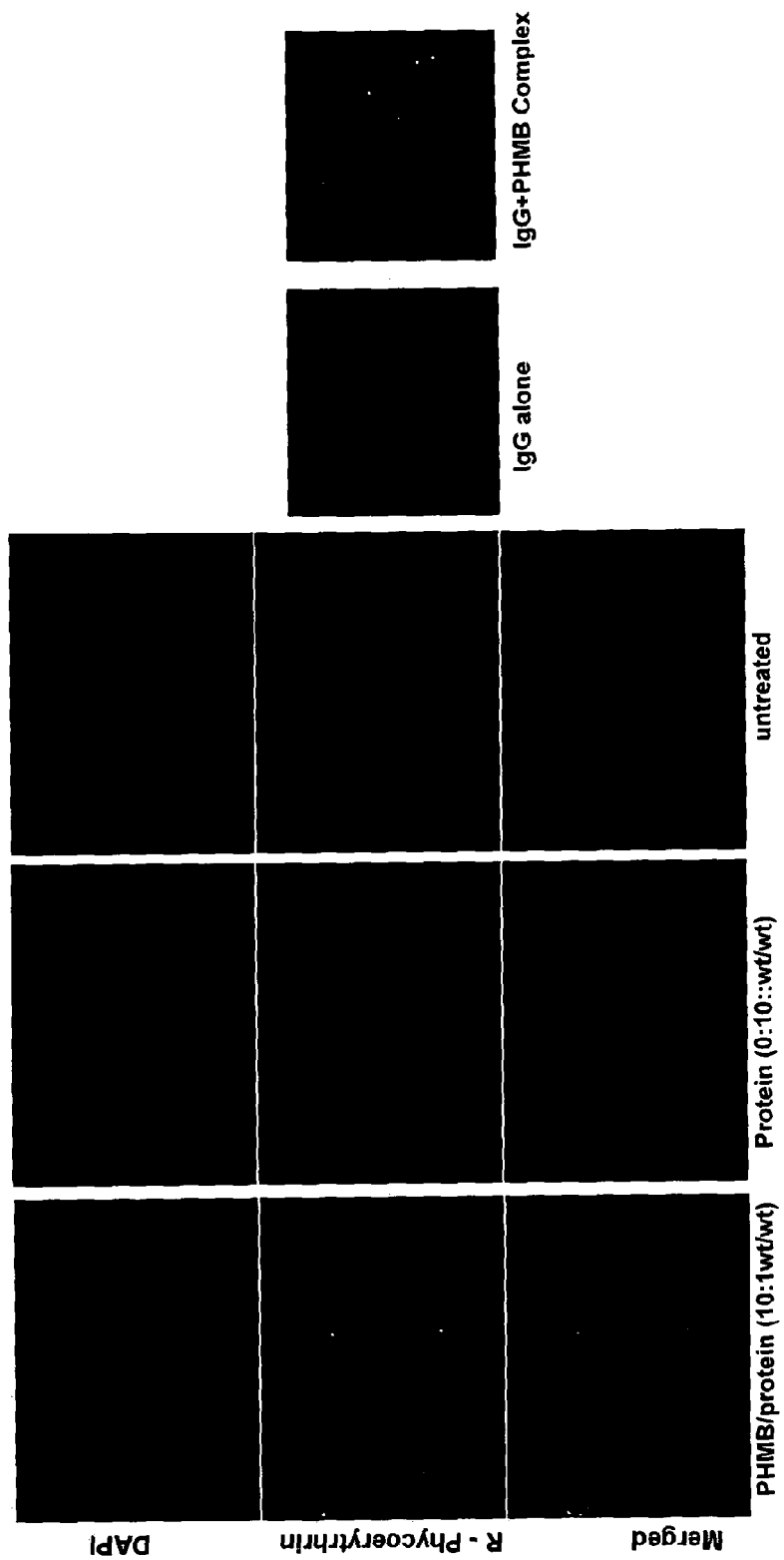

FIG. 35 PHMB mediated delivery of a red fluorescent protein and antibody (IgG-Alexa488) into human cells (HeLa)

3 µg of PHMB was mixed with 0.3 µg of fluorescent protein R—Phycoerythrin (panels at left) or alexa 488 labelled IgG antibody (panels at right) in 100 µl volume of PBS, allowed to stand for 30 minutes at room temperature. The resulting complex was diluted in 900 µl growth medium and the diluted complexes were overlayed on HeLa cells. After 2 hours of incubation cells were imaged using a fluorescence microscope.

Figure 36:
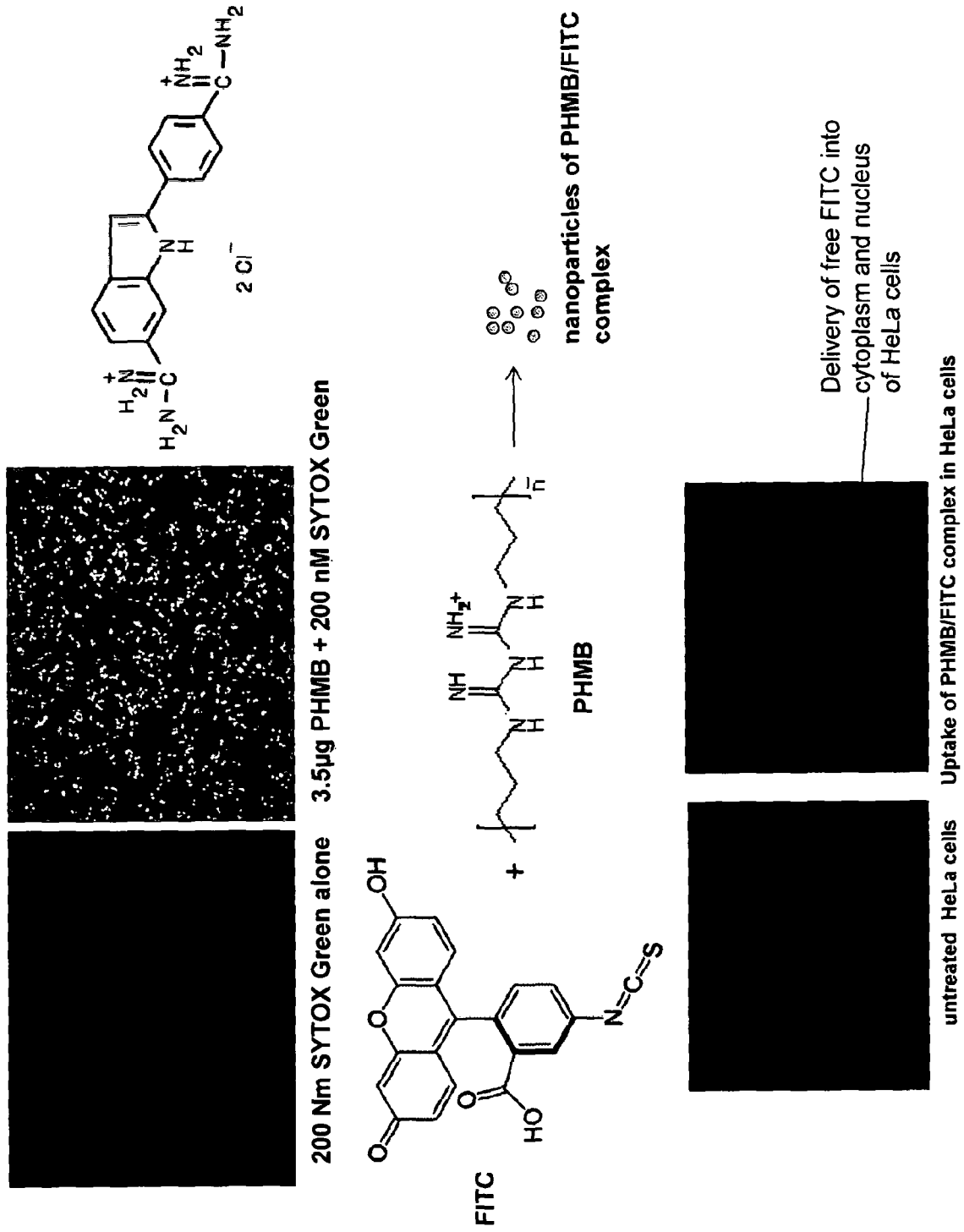

FIG. 36 PHMB mediated delivery of small fluorescent molecules into human cells (HeLa) 3.5 µg of PHMB was mixed with 1 µl of 100 µM small molecules (SYTOX Green or FITC) in 100 µl of PBS, allowed to stand for 30 minutes at room temperature. The resulting complexes were diluted with 900 µl growth medium and the diluted mixture was overlayed on HeLa cells, after 2 hours of incubation cells were imaged under fluorescence microscope.

Figure 37:
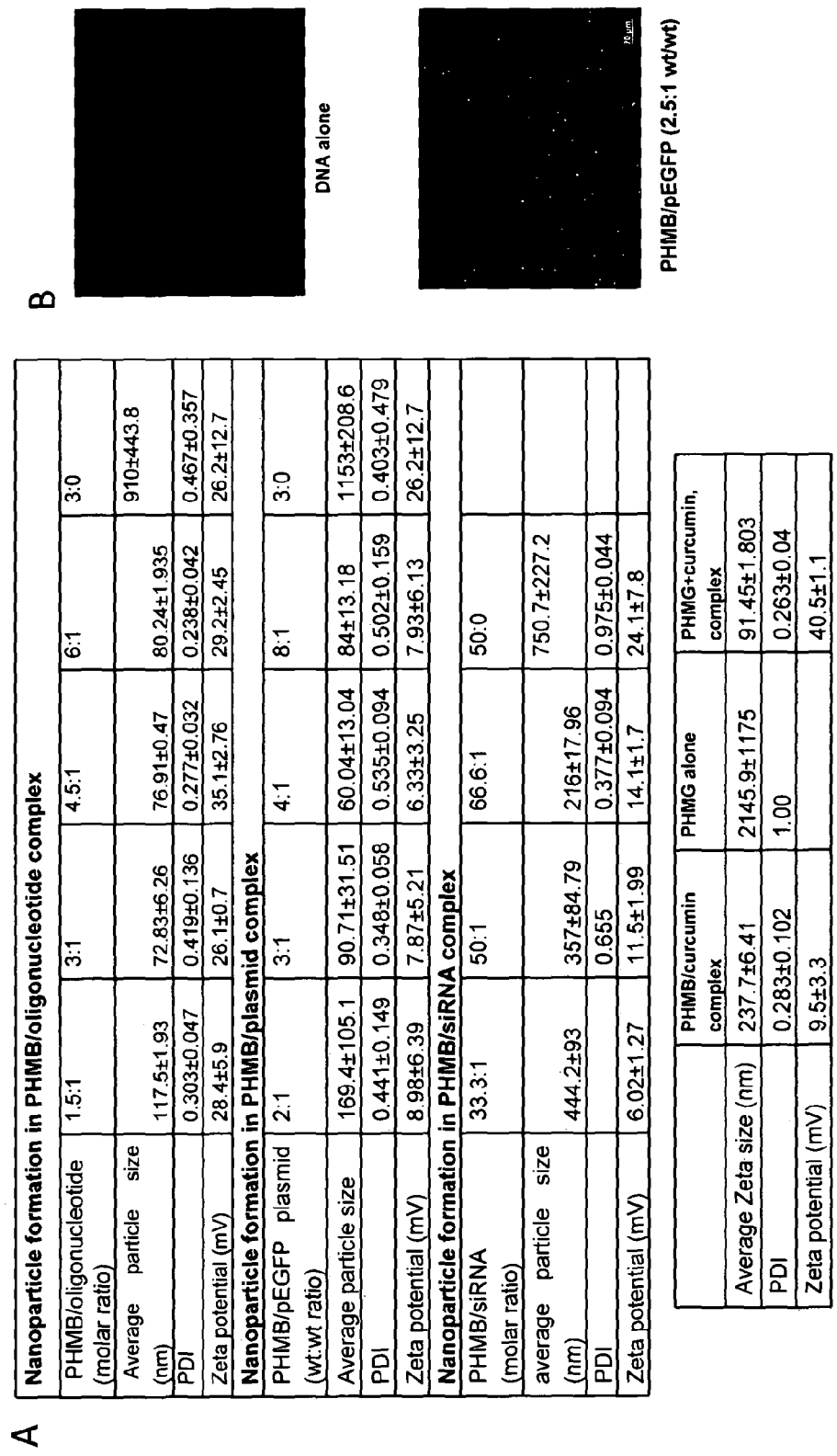

FIG. 37 PHMB forms nanoparticles with wide variety of cargo molecules

A. Characterization of nanoparticle formation by DLS. PHMB/oliognculeotides complex was prepared in 100 µl PBS by taking a fixed amount of oligonucleotides (1 µl of 100 µM stock) and varying the PHMB concentration (1-6 µg), incubated for 30 minutes at room temperature, resulting complex was diluted in 1 ml filtered water and average size, zeta potential were monitored using Zetasizer ZS nano. PHMB/pEGFP complex was prepared in 100 µl PBS by taking a fixed plasmid (1 µg) and varying the PHMB concentration (1-6 µg), as described above. PHMB/siRNA complex was prepared in 100 µl PBS by taking a fixed siRNA (1 µl of 100 µM stock) and varying the PHMB concentration (1-6 µg), as described above. For calculating molar concentration, average molecular weight of PHMB was taken as 3000 Daltons.

B. Characterization of nanoparticle formation by fluorescence microscopy. PHMB/pEGFP complex were prepared as described above, plasmid was stained with 100 nM SYBR Green and the complex were loaded on 1% agarose bed prepared on a glass slide and observed under fluorescence microscope using 490 nm Excitation, 520 nm emission. DNA alone doesn't show any particles, whereas PHMB/pEGFP complex appear as small particles.

Figure 38:
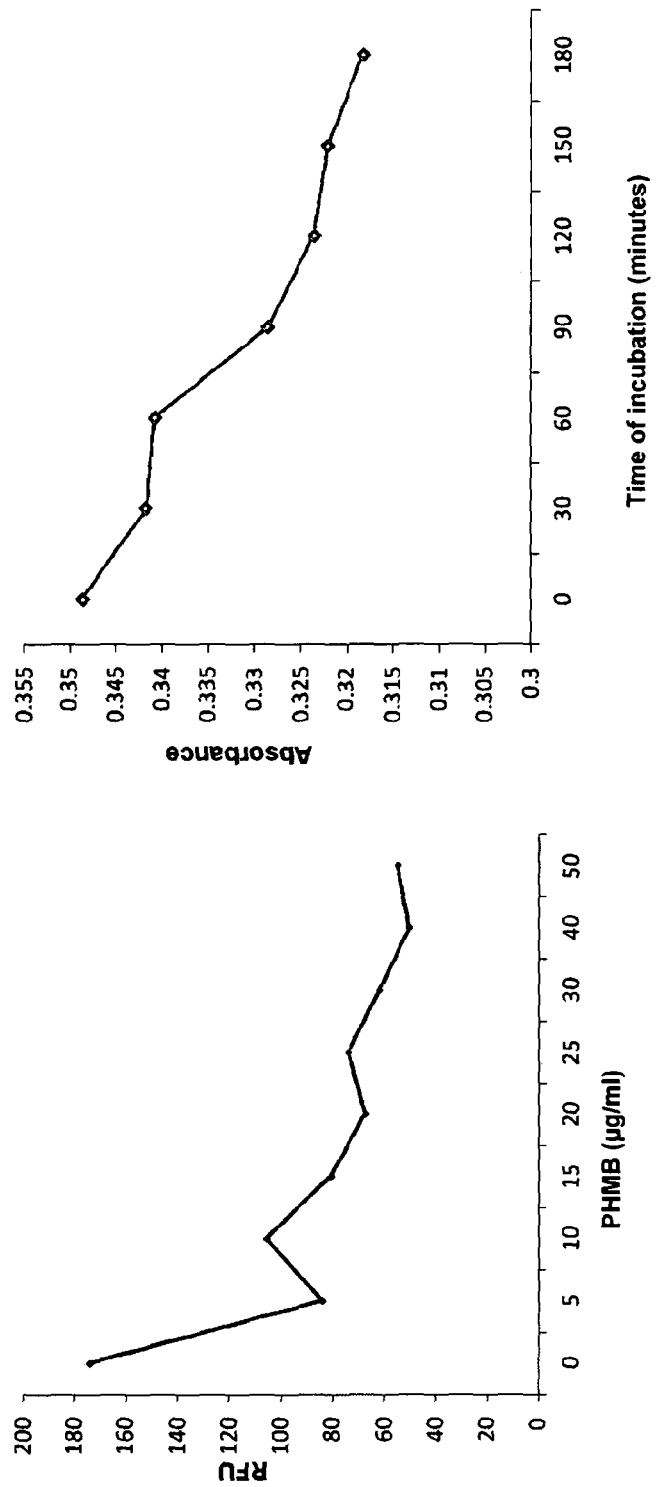

FIG. 38 PHMB interacts with the small molecule Nystatin

At left, Interaction of PHMB with Nystatin (10 units/ml), indicated by quenching, monitored by recording emission at 710 nm, upon excitation at 350 nm.

Figure 39:
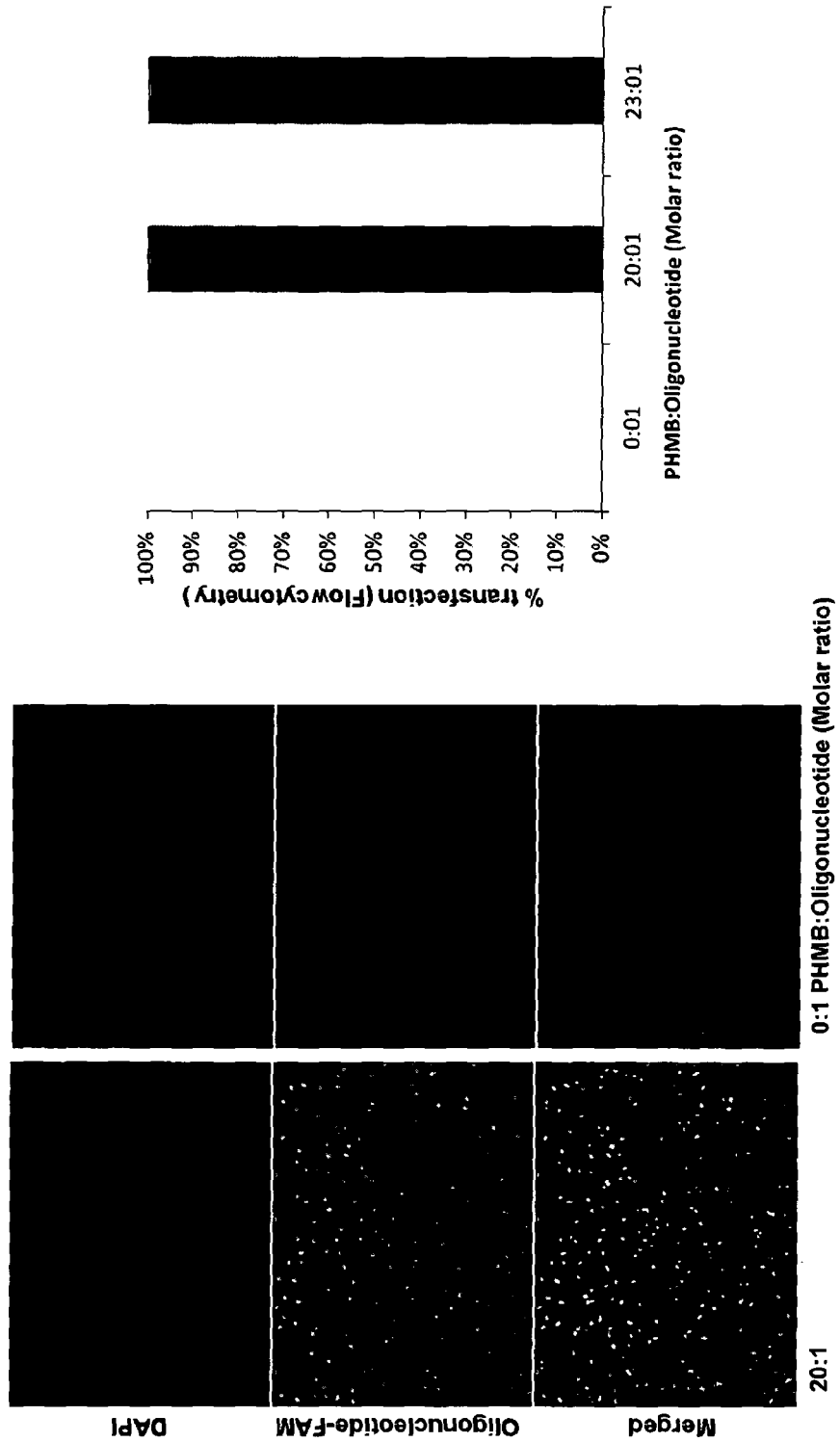

At right, Interaction of PHMB (3 mg) with Rifampicin (20 µg), indicated by reduced absorbance, monitored by the quenching in absorbance (470 nm) in presence of PHMB over a period of time FIG. 39 PHMB-mediated delivery of a fluorophore labelled DNA oligonucleotide into bacteria, *Salmonella enterica*

6 µg of PHMB was mixed with 1 µl of 100 µM 18 mer deoxyoligonucleotide labelled with 6 FAM in 100 µl volume of water with Ph12, allowed to stand for 30 minutes at room temperature. The resulting complex was diluted in 400 µl PBS, added to 100 µl of 0.20D *S. enterica* in early log phase, mixed well and incubated at 37° C. for 2 hours and counter stained with DAPI and observed under fluorescence microscope. Oligonucleotides delivery was quantified by flow cytometry.

Figure 40A:
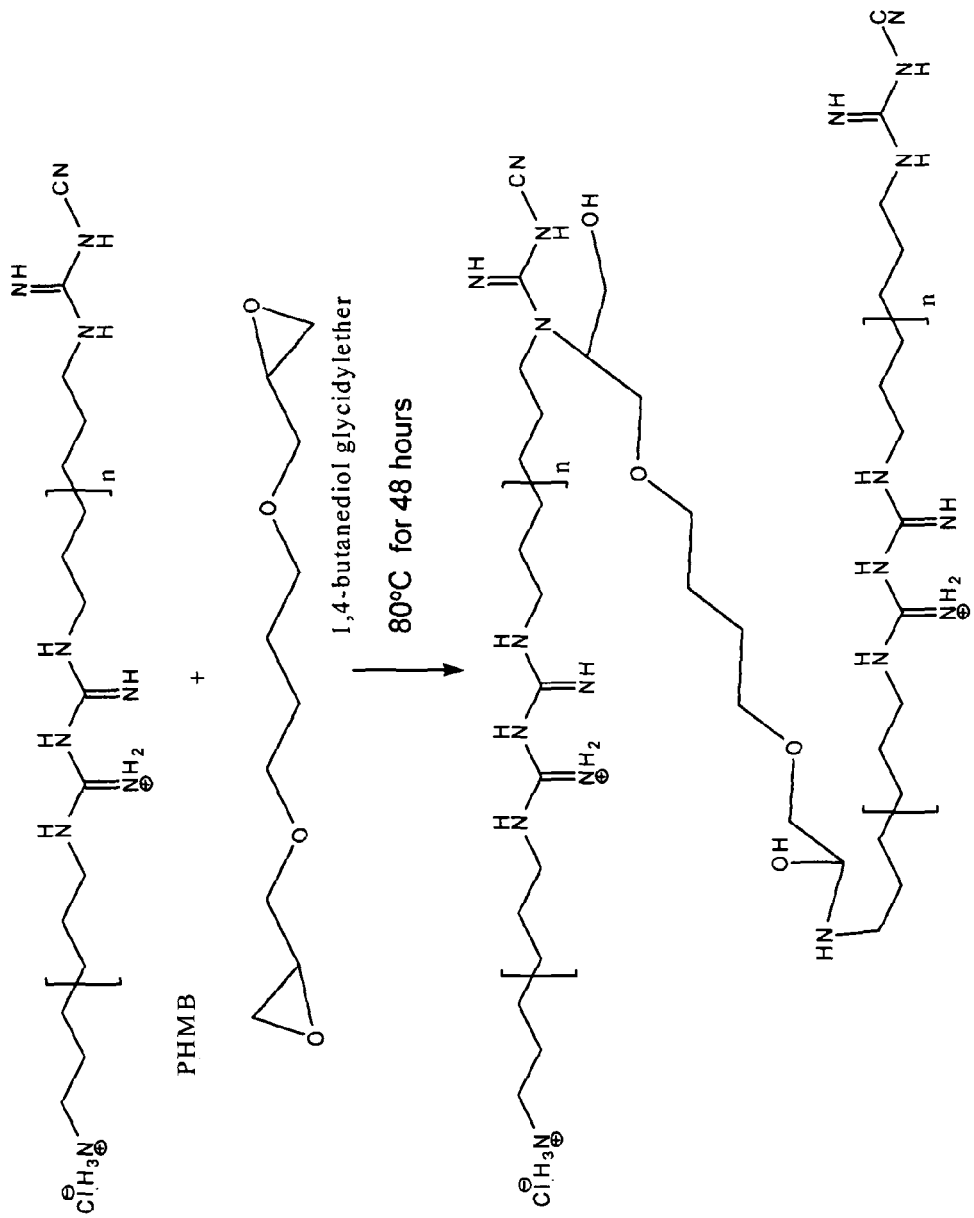
Figure 40B:
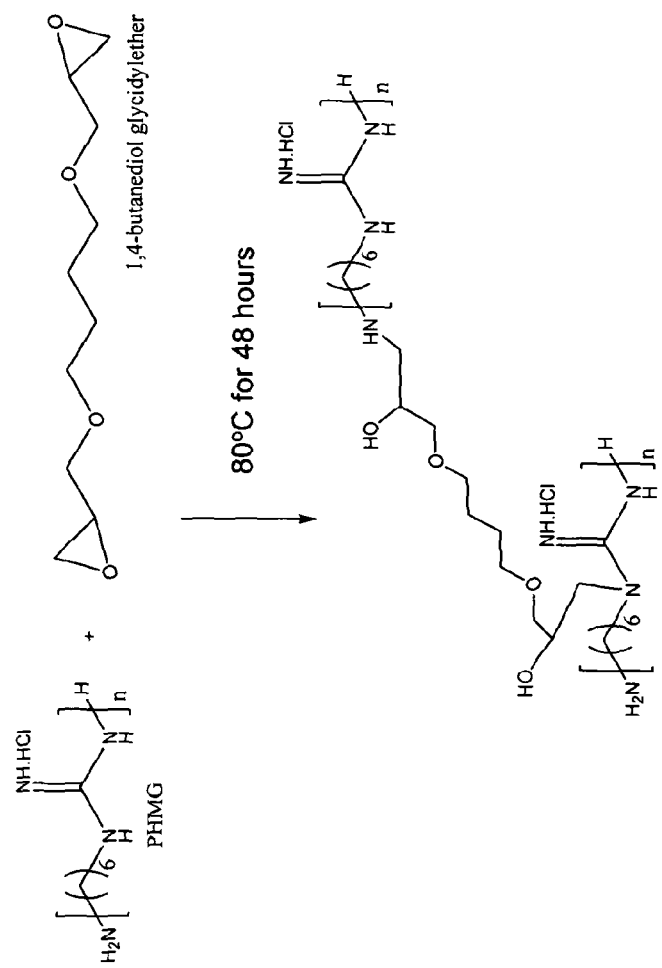
Figure 40C:
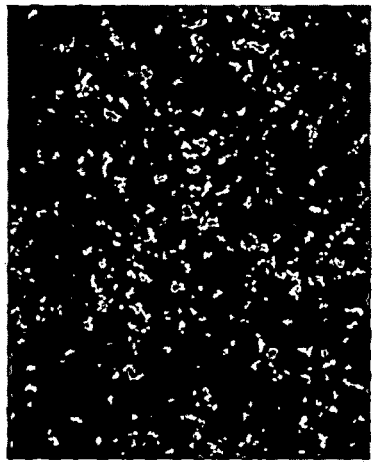
Figure 40C:

FIGS. 40a, 40b, and 40c. Branched PHMB/PHMG mediated delivery of GFP expressing plasmid DNA into human cells EXAMPLE 1: PHMB AND RELATED CATIONIC POLYMERS AS CARRIERS FOR DELIVERY INTO BACTERIA, FUNGI AND MAMMALIAN CELLS We have assessed PHMB and related molecules as carriers for delivery into prokaryotic and eukaryotic cells. No single technology has yet emerged as a practical gene transfer method for the clinic. Desirable qualities of a carrier include:

It should be able to interact with biomolecules
Enter on its own and as well as when loaded with biomolecules
Ability to release biomolecules upon entry
Low cytotoxic and suitable for in-vivo applications
High transfection efficiency for transient transfection is an important feature for research, as are low cytotoxicity, and effectiveness for difficult to transfect cells We considered that PHMB and related molecules may be able to act as effective carriers. Polyhexametheylenebiguanide (PHMB) is a cationic polymer with broad spectrum antimicrobial agent and less toxic to mammalian cells (Vantocil™ Arch biocides limited, UK). Low toxicity is an unusual and very beneficial property among delivery reagents and the low toxicity observed and safe track record of these compounds in a broad range of applications distinguishes this technology.

n=2 to 40, The weight-average molecular weight (Mw) and polydispersity for Bx529 VANTOCIL 100 are 3035 and 1.9 respectively. Such a Mw corresponds to an 'n' value of around 14 (more precisely 13.8). End groups: amine, guanidine and cyanoguanidine.

Polyhexametheylenemonoguanide (PHMG) is an analogue of PHMB with antimicrobial properties (Zhou et al., 2010).

Current uses of PHMB:
Used as an antiseptic, recommended choice in surgical wound dressings, (Stephen Gilliver2009)
present in disinfectants, swimming pool sanitizers, solid surface cleanser, mouth rinses and contact lens solutions (Lucas et al., 2009)
Used in treatment of hatching eggs, as a deodorizer and preservative in cosmetics, textiles and treatment of cooling systems to prevent *Legionella* growth etc We considered that PHMB may be useful as a carrier, either as a covalent conjugate or as a non-covalent complex, possibly with hydrophobic and/or electrostatic interactions. If this were to be the case, other properties of PHMB may enhance its use as a carrier. The toxicity profile of PHMB is well studied (Muller et al., 2008; Kathryn V. Montague, 2004) and PHMB is considered to be a poor allergen (a desirable property) from tests in human patients, (Schnuch et al., 2007). The antimicrobial properties may also be advantageous in reducing the problem of contamination in cell culture.

Uptake of free PHMB-FITC into three kingdoms was assessed:
  a) Bacteria:
  Gram negative: *E. coli* and *S. enterica*
  Gram positive: *S. aureus*
  Acid fast: *M. smegmatis*
  b) Fungi: *Aspergillus fumigatus*
  c) Mammalian cells: macrophages, monocytes, HEK and HeLa cells See FIGS. 2 to 12, FIG. 33 for conjugation of PHMB with FITC Evidence for interaction of PHMB with nucleic acids in-vitro (Essential for a carrier to form a noncovalent complex with cargo and deliver it into cells)

See FIGS. 13 to 17.

Free PHMB enters into a wide variety of cells. PHMB interacts with nucleic acids. Can PHMB also carry nucleic acids and analogues? Yes: See FIGS. 18 to 21, FIG. 39.

Are the delivered nucleic acids available for effective function? Yes: see FIGS. 22 to 25

PHMB analogue also possess cell penetrating properties: see FIGS. 26 to 27

Effect on primary cells: See FIGS. 28 to 30

Analogues: see FIGS. 31 to 32 and 40, (Note, the chemical formulae in FIG. 32 are adopted from F. C. Krebs et al./*Biomedicine &Pharmacotherapy* 59 (2005) 438-445).

EXAMPLE 2 USE OF PHMB AND RELATED CATIONIC POLYMERS FOR SMALL MOLECULE DELIVERY INTO MAMMALIAN CELLS

We have shown that PHMB and related cationic polymers can interact with small molecules (for example Nystatin, Rifampicin, curcumin, free FITC, SYTOX Green) and deliver them into mammalian cells, for example HeLa. See FIG. 31, 36 to 38. Also, we observed synergistic bacterial killing using PHMB/rifampicin complexes that were formed prior to exposure to bacterial cells.

EXAMPLE 3 USE OF PHMB AND RELATED CATIONIC POLYMERS FOR PROTEIN DELIVERY INTO MAMMALIAN CELLS

PHMB and analogues were able to deliver protein molecules (for example R-phycoerythrin or alexa 488 conjugated IgG antibodies) into mammalian cells such as HeLa cells, see FIG. 35.

EXAMPLE 4. PHMB FORMS COMPLEXES WITH NUCLEIC ACID MOLECULES RAPIDLY AND HIGH PH ENHANCES TRANSFECTION EFFICIENCY

Our method shows that higher transfection efficiency of nucleic acids can be achieved when carrier and cargo are complexed in buffers with high pH (13.5-10). We tested the amount of time required for complex formation between PHMB and nucleic acids, Our results show that as little as five minutes is sufficient to form complex which can enter mammalian cells or even allowing the complex to stay for hours at room temperature will not compromise the transfection capacity. See FIG. 34.

EXAMPLE 5: USE OF PHMB AND RELATED CATIONIC POLYMERS TO FORM NANOPARTICLES WITH BIOACTIVE MOLECULES

We have assessed PHMB and related molecules as a means to form nanoparticles with a range of bioactive molecules. No single technology has yet emerged as a practical nanoparticle formation method for the clinic Desirable qualities of a carrier include:
  Efficient nanoparticle formation using simple procedures
  Useful with a range of bioactive molecules
  Ability to release biomolecules for bioactive effects
  Low cytotoxic and suitable for in-vivo applications We observed while investigating the cell delivery properties of PHMB and related molecules that these polymers are able to effectively form nanoparticles with a range of molecules, many of which are bioactive. The use of bioactive molecules may benefit from inclusion within nanoparticles prior to further formulation and application. Such benefits could include improved solubility, improved stability, protection against degradation during use and improve or altered distribution or clearance properties in vivo. Low toxicity is an unusual and very beneficial property among nanoparticle forming reagents and the low toxicity observed and safe track record of these compounds in a broad range of applications over several decades of wide usage distinguishes this technology.

Nanoparticle Formation with a Range of Bioactive Molecules was Assessed

Evidence for interaction of PHMB with nucleic acids in-vitro, which is essential for a carrier to form a noncovalent complex and nanoparticle with cargo molecules and deliver it into cells.

Evidence for complex formation was assessed using a range of methods See FIGS. 13 to 17 and 38.

Dynamic light scattering (DLS) and fluorescence microscopy were used to measure the formation of nanoparticles. Evidence of nanoparticle formation was assessed using a range of molecules.
  a) nucleic acids, including chromosomal DNA, plasmid DNA and RNA
  b) proteins
  c) small molecules Our results show that PHMB and related molecules form nanoparticles with wide variety of cargo molecules. See FIGS. 31 and 37.

CONCLUSIONS

Free PHMB is able to enter a wide variety of bacteria, fungi and mammalian cells (three kingdoms demonstrated)

PHMB and analogues are potent carriers for all cell types, with large potential applications as a carrier for mammalian systems PHMB and analogues interact with protein and peptides PHMB interacts with a range of small organic molecules including both basic and acidic small molecules.

PHMB and analogues are capable of carrying nucleic acids into the nucleus of mammalian cells and presumably release them for effective function inside cells Very low toxicity is reported and observed for PHMB and analogues PHMB and analogues are capable of carrying proteins, peptides and small molecules (example SytoxGreen and free FITC) into mammalian cells.

PHMB and analogues are capable of carrying nucleic acids, peptide nucleic acids and small molecules into bacteria and fungi.

The substance cost is very low

Chemistry allows further modifications

Complexation of PHMB with nucleic acids under high pH results in more efficient nucleic acid delivery into bacteria and mammalian cells.

PHMB and analogues complex with nucleic acids very rapidly in minutes and complex are stable for hours at room temperature PHMB and analogues are able to form nanoparticles with a range of bioactive molecules.

REFERENCES

Gilliver et al (2009) *J Wound Care/ACtiva Healthcare Supplement* 9-14 PHMB: a well-tolerated antiseptic with no reported toxic effects Müller & Kramer (2008) *J Antimicrobial Chemotherapy* 61, 1281-1287 Biocompatibility index of antiseptic agents by parallel assessment of antimicrobial activity and cellular cytotoxicity Schnuch et al (2007) *Contact Dermatitis* 56, 235-239 The biocide polyhexamethylene biguanide remains an uncommon contact allergen.

Kathryn V. Montague (2004). Reregistration Eligibility Decision (RED) for PHMB. United states environmental protection agency. Washington, D.C. 20460. (epa.gov/oppsrrd 1/REDs/phmb_red.pdf)

Lucas et al (2009) *Talanta* 80, 1016-1019. Analysis of polyhexamethylene biguanide in multipurpose contact lens solutions.

The invention claimed is:

1. A method for promoting entry of an introduced agent into a cell, the method comprising the step of exposing the cell to non-covalently complexed nanoparticles comprising the introduced agent and an entry-promoting agent, wherein the entry-promoting agent comprises polyhexamethylene biguanide (PHMB), and wherein the agent to be introduced and the entry promoting agent are mixed together at a pH of 10-13.5.

2. The method of claim 1, wherein the cell is a prokaryotic cell.

3. The method of claim 1, wherein the cell is a eukaryotic cell, optionally in a tissue or organ.

4. The method of claim 1, wherein the cell is a mammalian cell.

5. The method of claim 1, wherein the introduced agent comprises a small molecule.

6. The method of claim 1, wherein the introduced agent comprises a polypeptide.

7. The method of claim 1, wherein the introduced agent comprises a nucleic acid or nucleic acid analogue.

8. The method of claim 1, wherein the method is performed in vitro.

9. The method of claim 1 wherein the method is performed in vivo.

10. The method of claim 1, wherein the method is performed ex vivo.

11. The method of claim 1, wherein the method is performed with from up to 100-fold molar excess of introduced agent over entry-promoting agent to up to 1000-fold molar excess of entry-promoting agent over introduced agent.

12. The method of claim 1, wherein the entry promoting agent and introduced agent have been mixed together or incubated or are provided together in a buffer.

* * * * *